United States Patent
Gefen et al.

(10) Patent No.: US 7,951,102 B2
(45) Date of Patent: May 31, 2011

(54) CERVICAL COLLAR

(75) Inventors: Amit Gefen, Ganei Tikva (IL); Michal Peleg Lubovsky, Mevaseret Zion (IL); Omri Lubovsky, Mevaseret Zion (IL)

(73) Assignees: Hadasit Medical Research and Development Ltd., Jerusalem (IL); Ramot At Tel Aviv University Ltd., Tel Aviv (IL)

(\*) Notice: Subject to any disclaimer, the term of this patent is extended or adjusted under 35 U.S.C. 154(b) by 842 days.

(21) Appl. No.: 10/572,946

(22) PCT Filed: Sep. 20, 2004

(86) PCT No.: PCT/IL2004/000870
§ 371 (c)(1),
(2), (4) Date: Nov. 20, 2006

(87) PCT Pub. No.: WO2005/027803
PCT Pub. Date: Mar. 31, 2005

(65) Prior Publication Data
US 2007/0118060 A1 May 24, 2007

(30) Foreign Application Priority Data
Sep. 21, 2003 (IL) .......................... 158036

(51) Int. Cl.
*A61F 5/00* (2006.01)

(52) U.S. Cl. .................. 602/18; 128/DIG. 23
(58) Field of Classification Search .................. 602/18, 602/5, 17, 15, 57; 5/637; 606/57; 128/DIG. 23, 128/845, 846, 857, 858, 869, 870
See application file for complete search history.

(56) References Cited

U.S. PATENT DOCUMENTS

| | | |
|---|---|---|
| 5,048,509 A | 9/1991 | Grundei et al. |
| 5,575,763 A * | 11/1996 | Nagata et al. .......... 602/18 |
| 5,682,632 A | 11/1997 | Cotroneo |
| 5,785,058 A | 7/1998 | Reynolds |

\* cited by examiner

*Primary Examiner* — Michael A. Brown
(74) *Attorney, Agent, or Firm* — Browdy and Neimark, PLLC

(57) ABSTRACT

The present invention discloses a novel cervical collar for maintaining the airways in head and neck immobilized trauma patient open. This collar comprises a rigid motion-restricting frame (220, 230, 240, 270, 280) attached to the head (100); and, a jaw clasp (210, 290) attached to the jaw (110). The collar is simultaneously restricting the motion of the head (100) and neck while allowing motion of the jaw (110) to maintain open airways. A jaw clasp (290) useful for performing the jaw-thrust maneuver motion of the jaw (110) to maintain open airways is also presented. Said device comprising a plurality of movable fitting elements adapted to fit the jaw (110) tightly; and, a plurality of movable mover elements adapted to move the jaw (110).

3 Claims, 43 Drawing Sheets

Figure 10A:
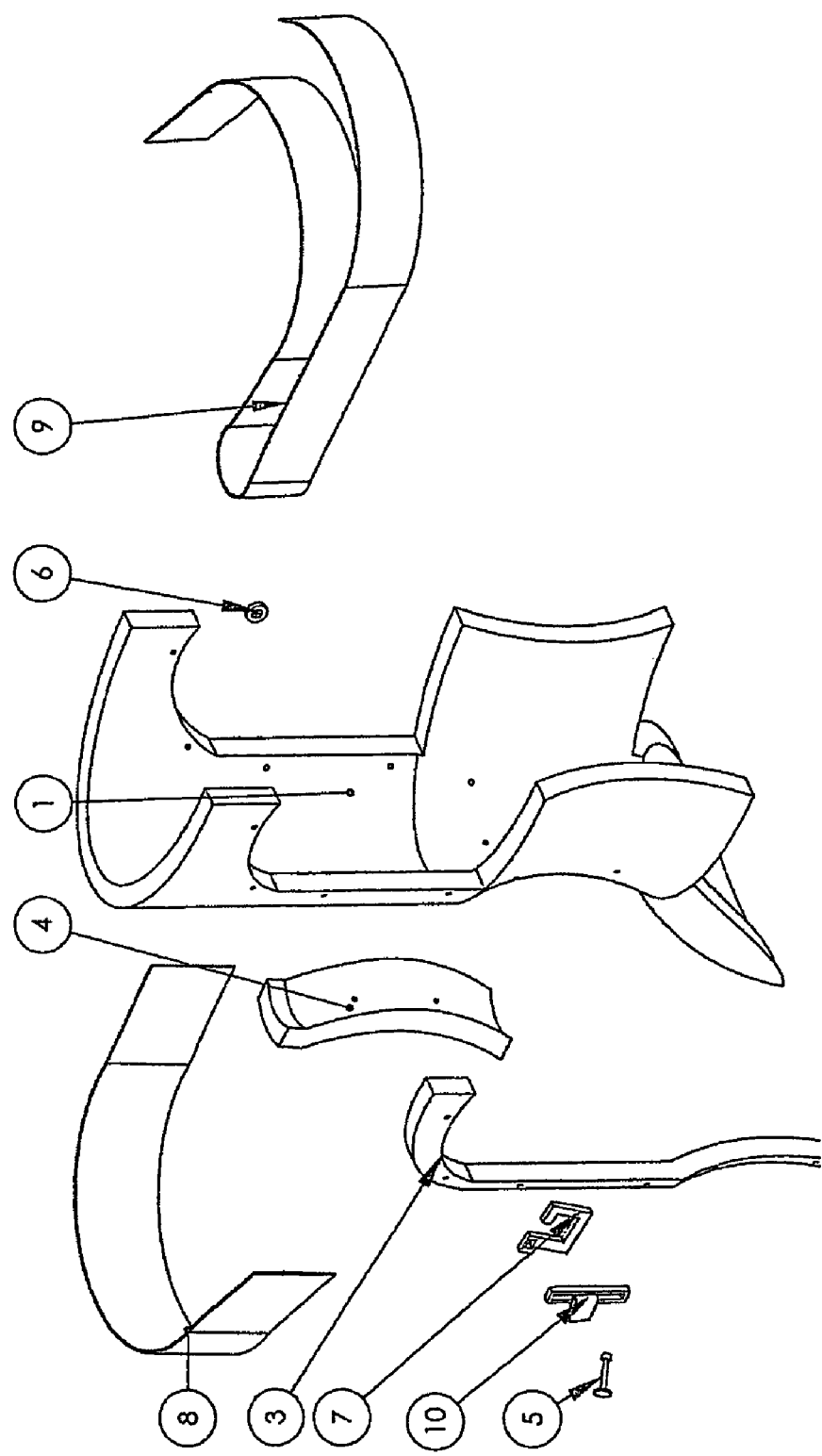

| Label in FIG 10A | Detailed Figure Or Function | Quantity |
| --- | --- | --- |
| 1 | 11 | 1 |
| 2 | 12 | 1 |
| 3 | 13 | 1 |
| 4 | 14 | 14 |
| 5 | 15 | 14 |
| 6 | 16 | 4 |
| 7 | 17 | 2 |
| 8 | Connecting Strap | 1 |
| 9 | Forehead Starp | 1 |
| 10 | Forehead Loop | 1 |

FIG. 10C

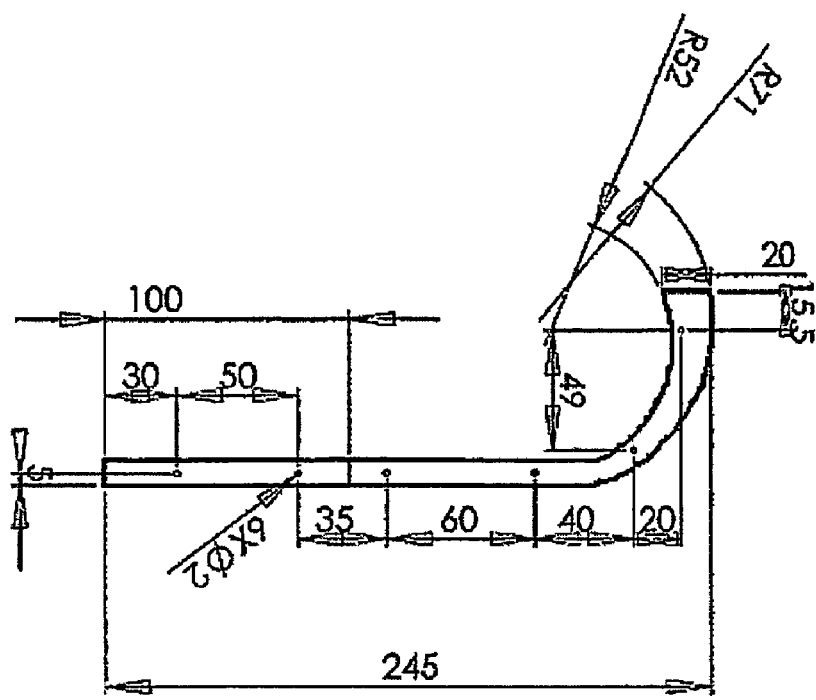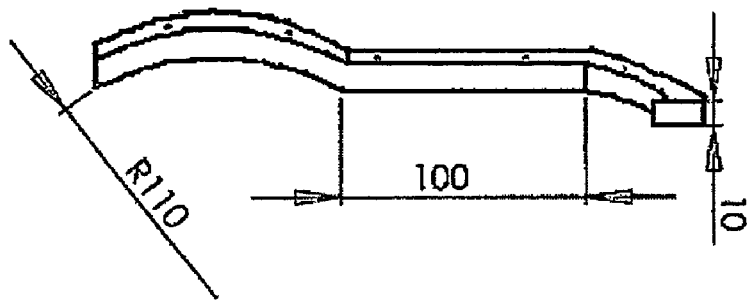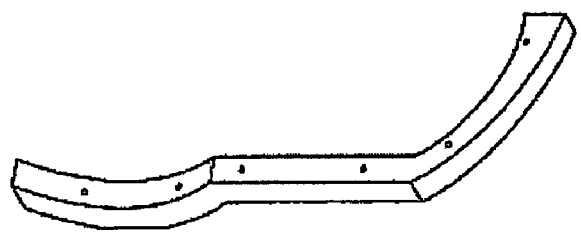
FIG. 12

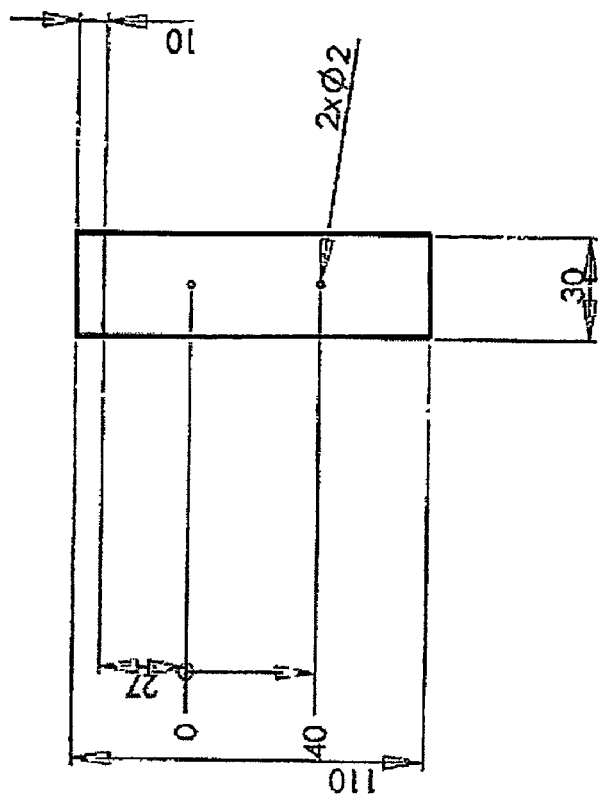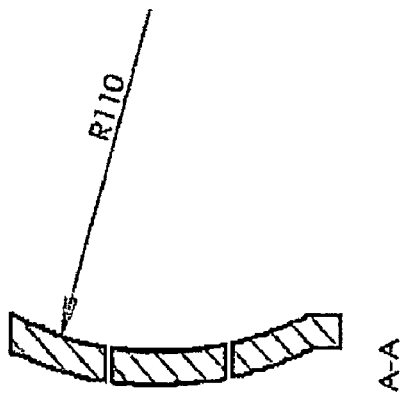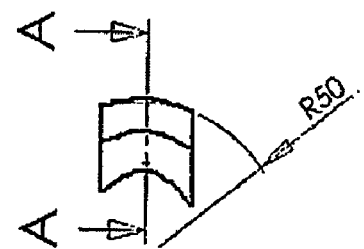
FIG. 14

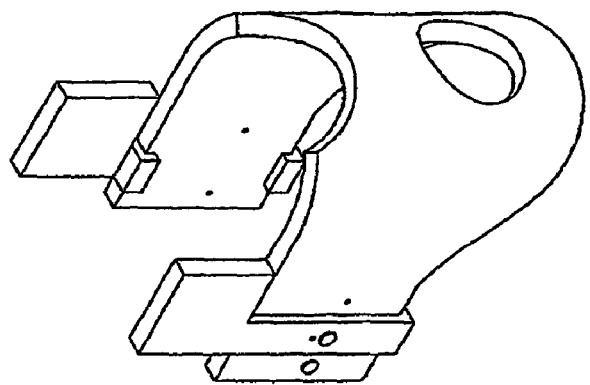
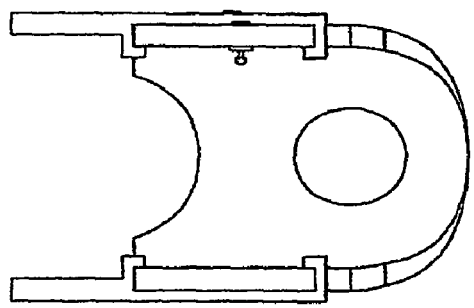
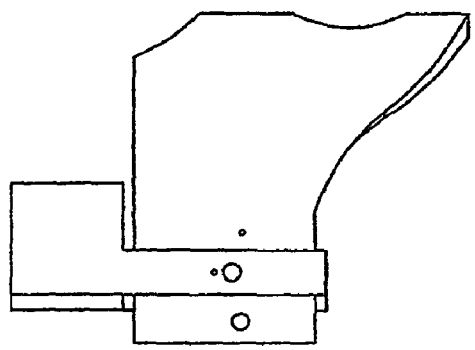
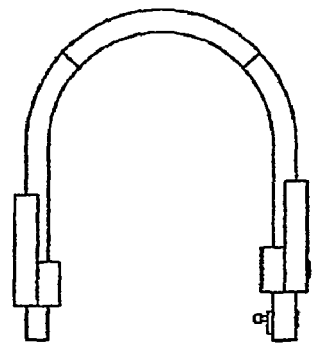
FIG. 18B

Figure 18A:
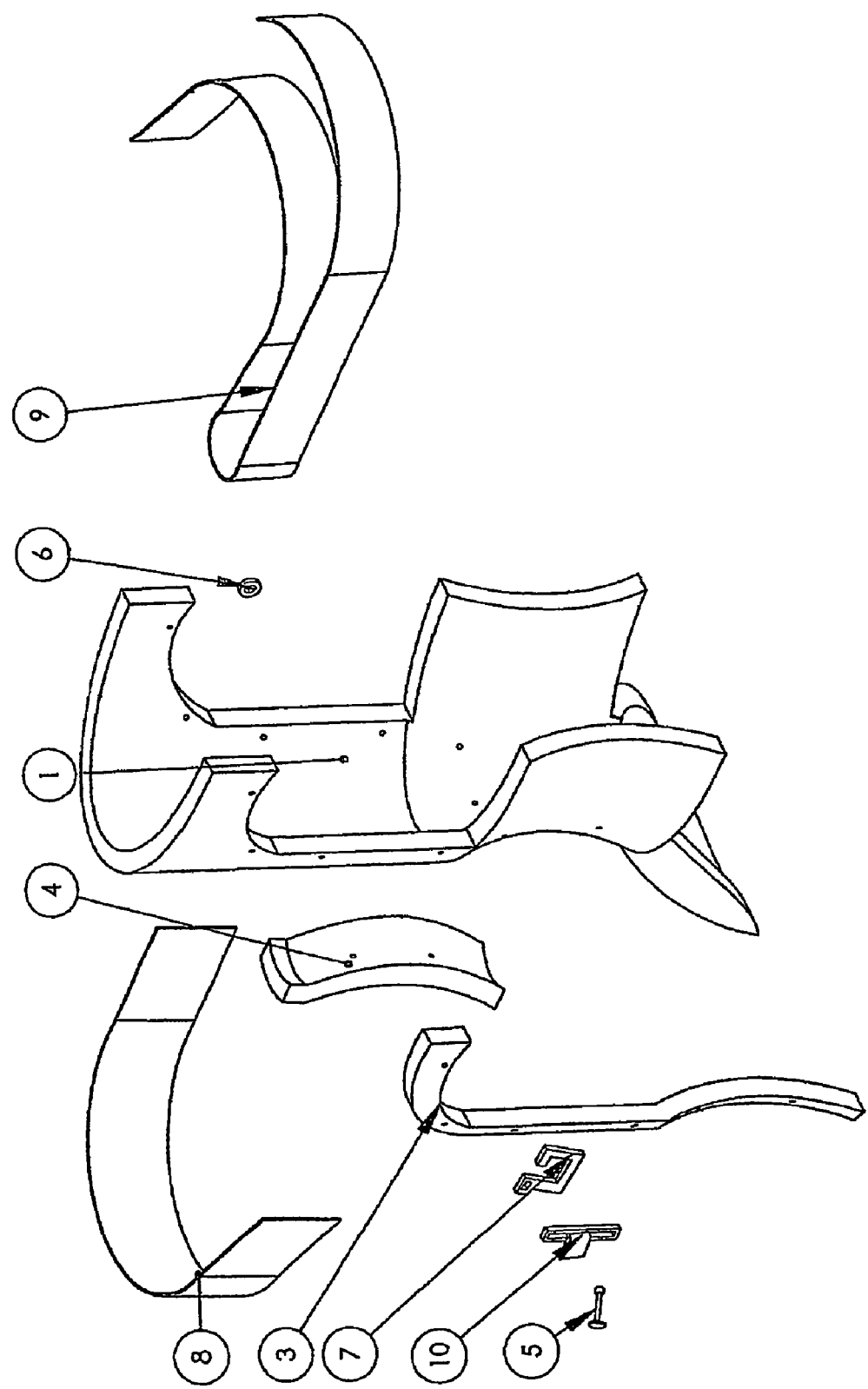

| Label in FIG 18A | Detailed Figure | Quantity |
|---|---|---|
| 1 | 19 | 1 |
| 2 | 20 | 1 |
| 3 | 21 | 1 |
| 4 | 22 | 4 |
| 5 | 15 | 4 |
| 6 | 16 | 4 |
| 7 | Connecting Strap | 2 |
| 8 | Lower Strap | 1 |
| 9 | Lower Loop | 1 |

FIG. 18C

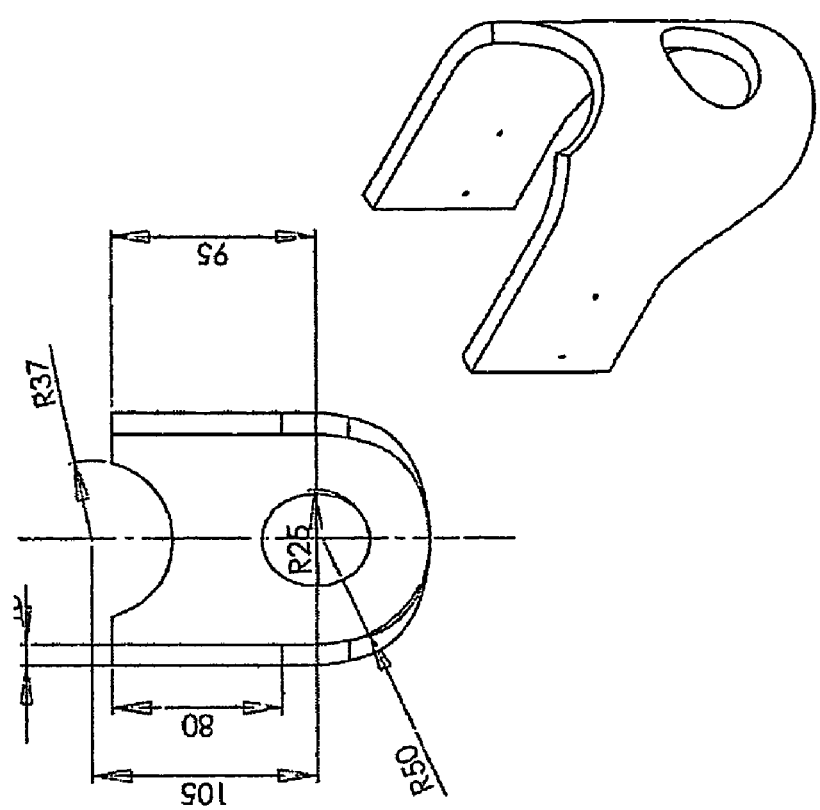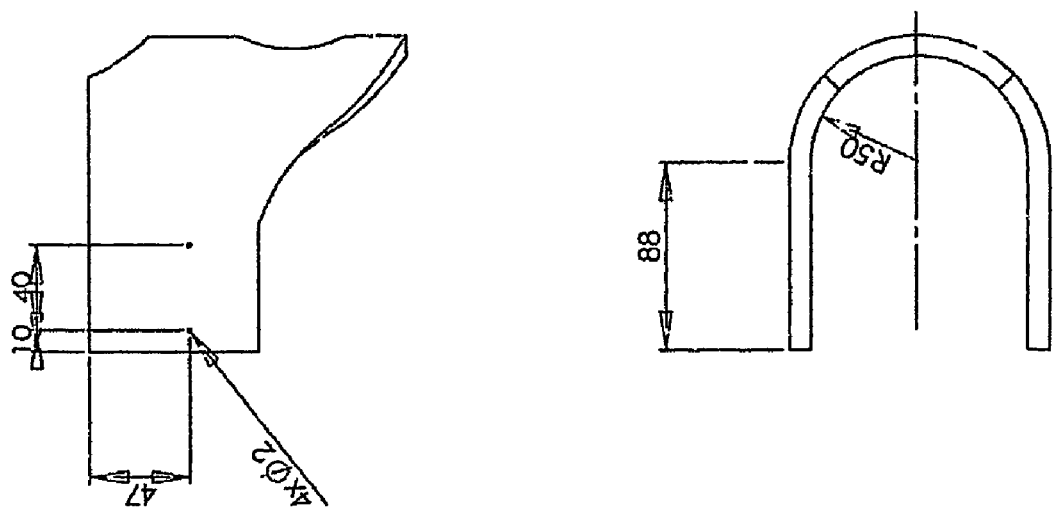
FIG. 19

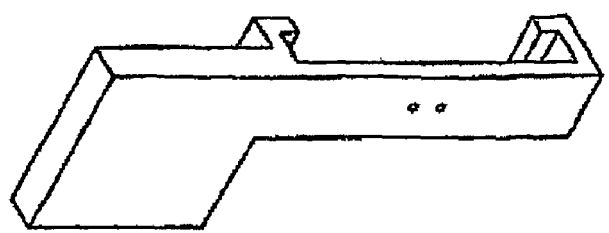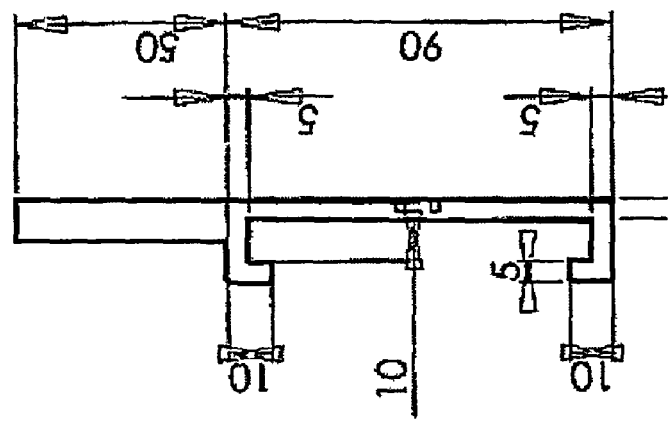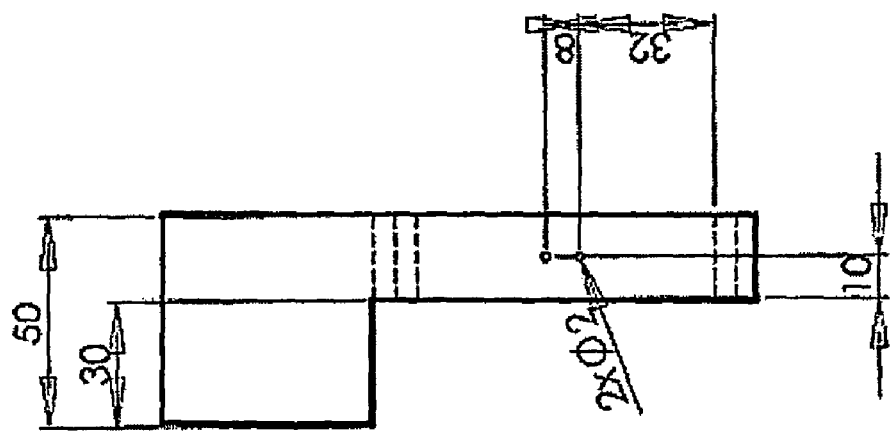
FIG. 20

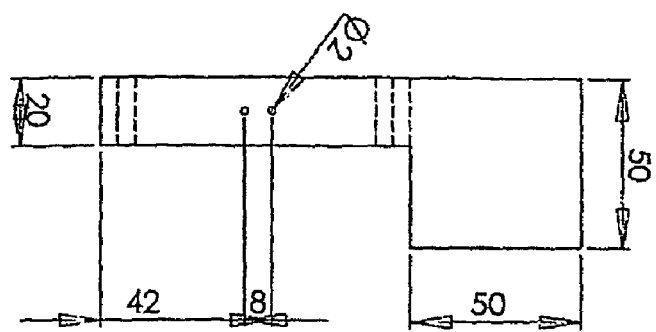
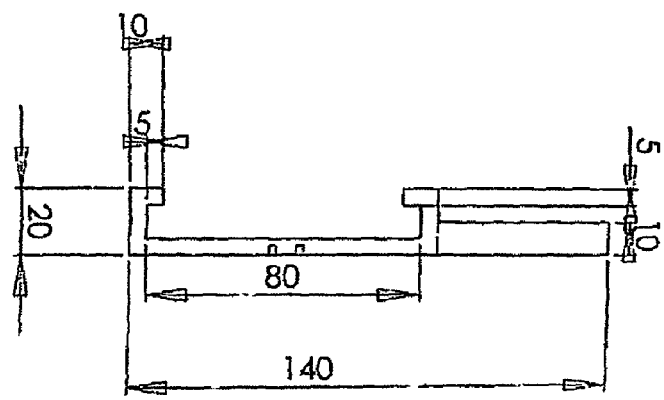
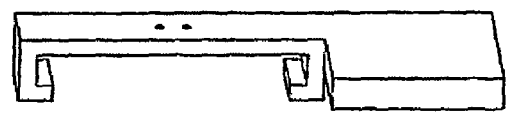
FIG 21

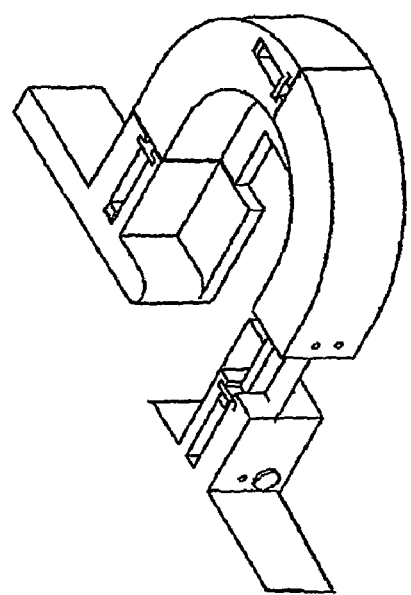
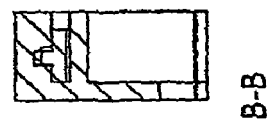
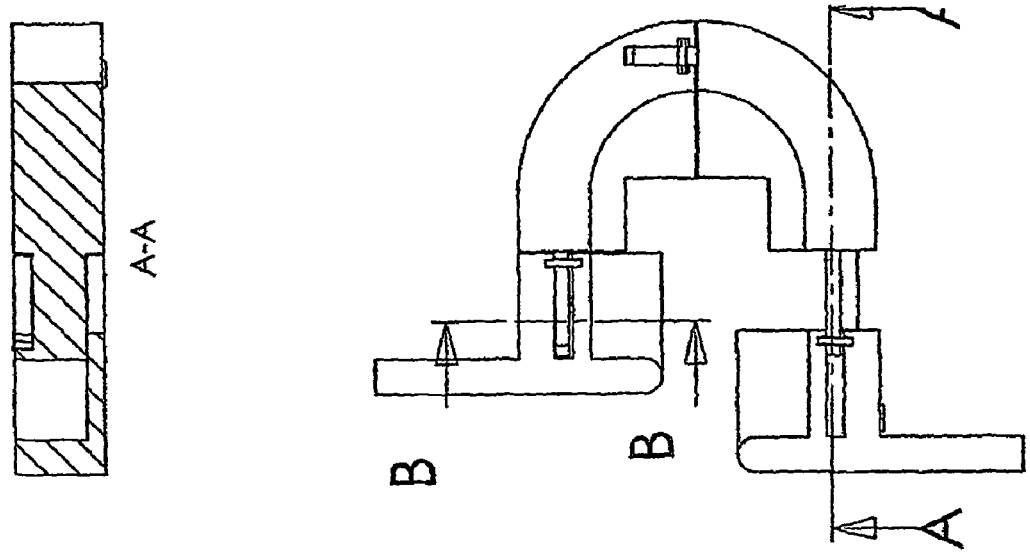
FIG. 22B

Figure 1:
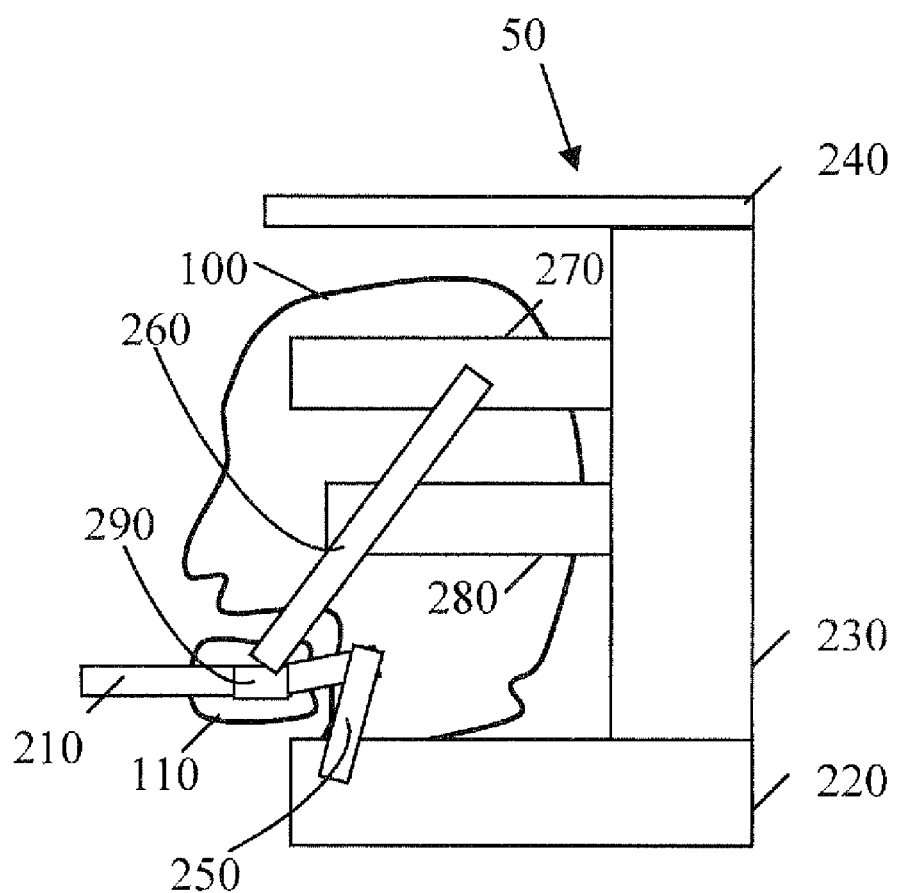

| Label in FIG 20A | Detailed Figure Or Function | Quantity |
|---|---|---|
| 1 | 31A 31B | 1 |
| 2 | 32A 32B | 1 |
| 3 | 33A 33B | 1 |
| 4 | 34A 34B | 1 |
| 5 | 35 | 3 |
| 6 | 36 | 16 |
| 7 | 260 of FIG 1 | 2 |
| 8 | Strap | 3 |
| 9 | Loop | 3 |
| 10 | Padding | 2 |

FIG. 22C

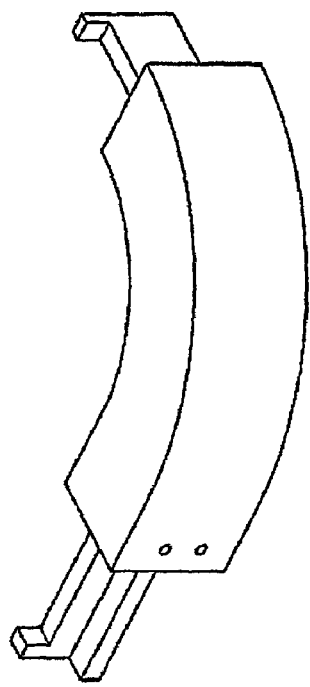
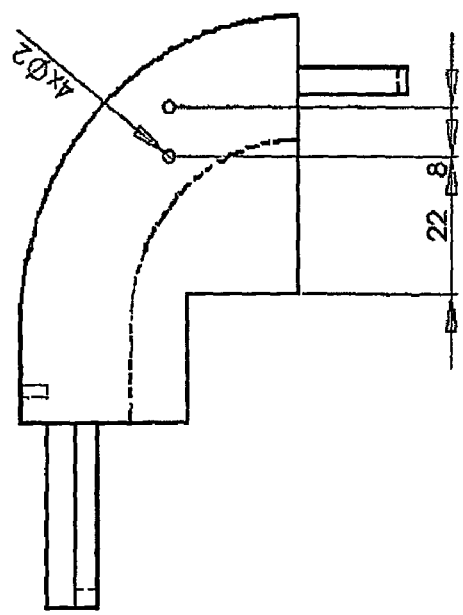
FIG. 23B

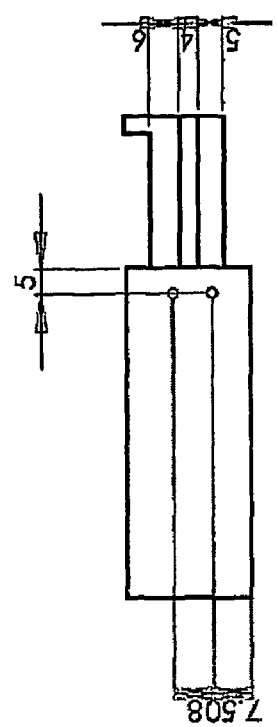
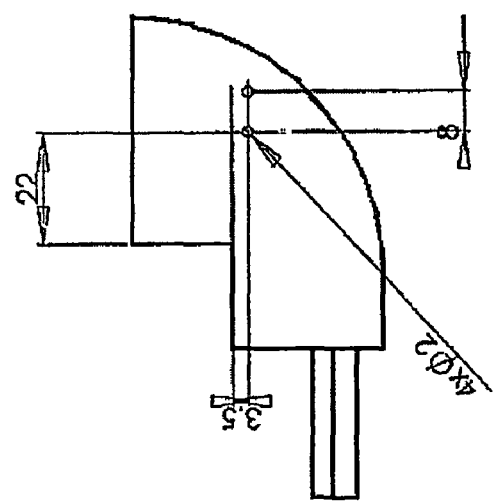
FIG. 24B

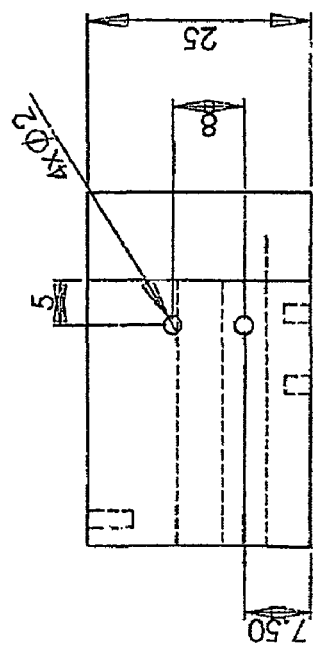
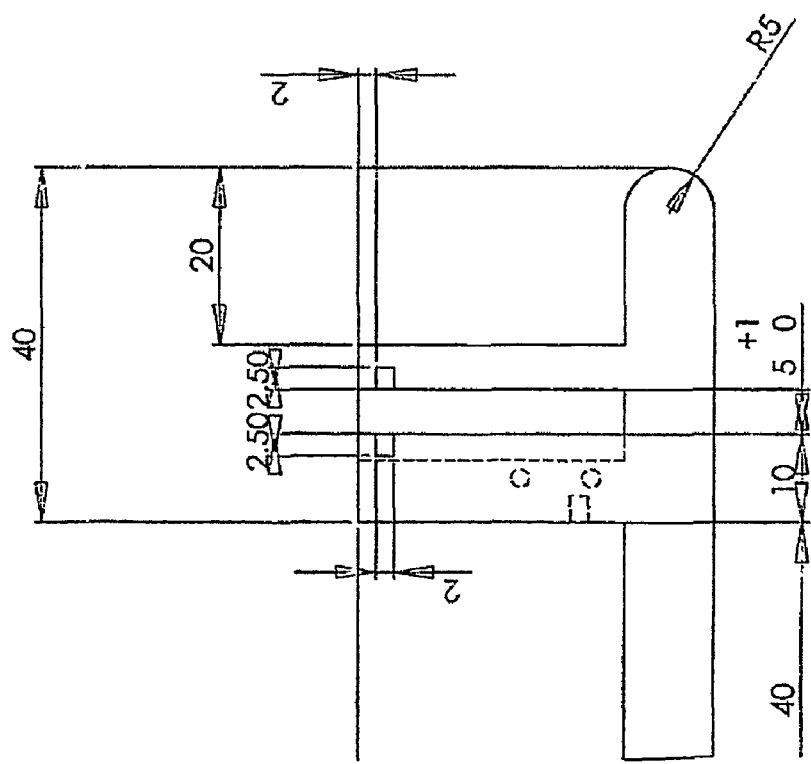
FIG. 25A

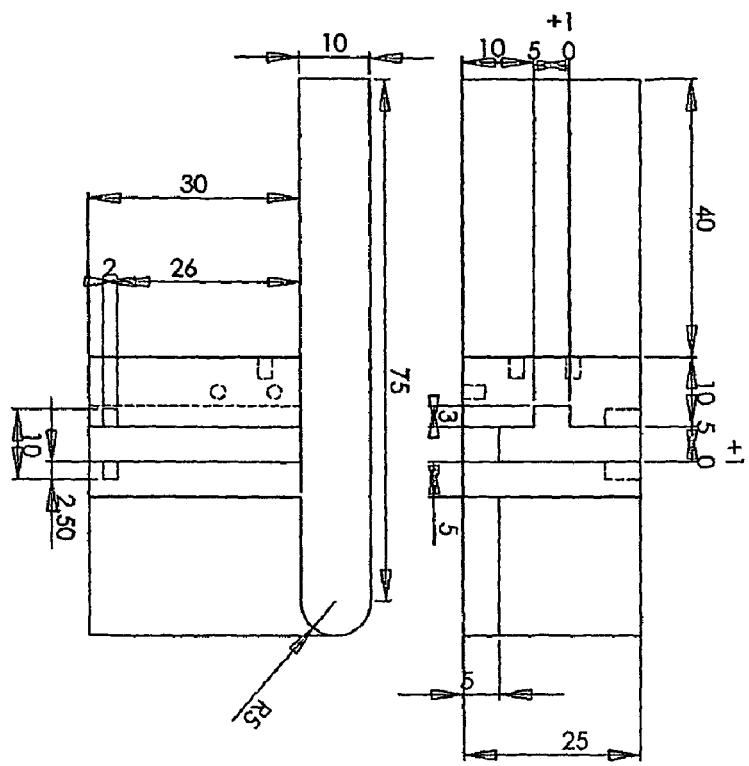
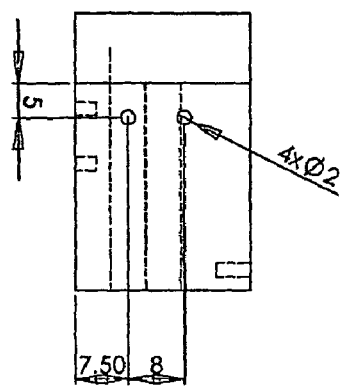
FIG. 26A

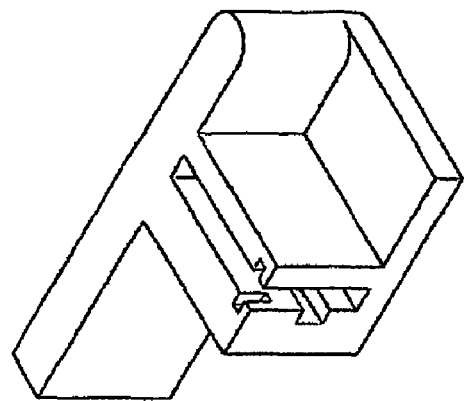
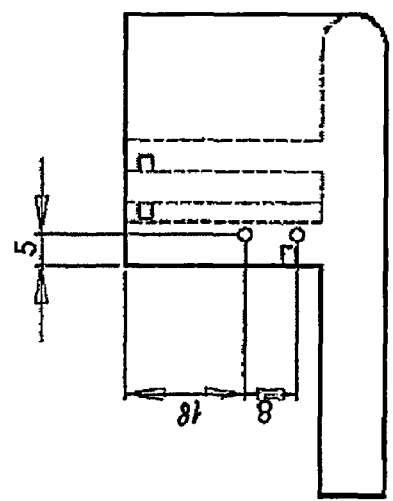
FIG. 26B

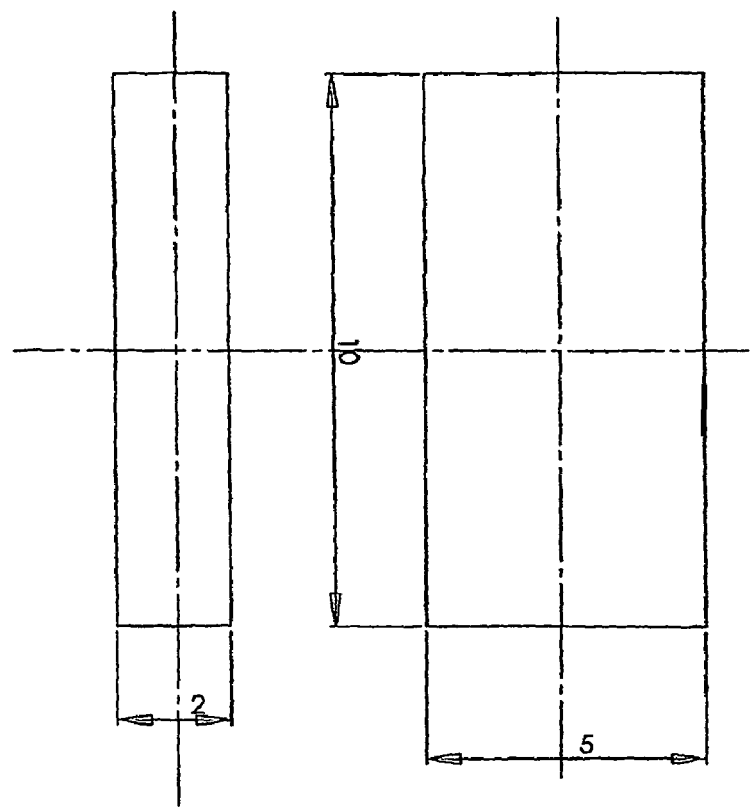
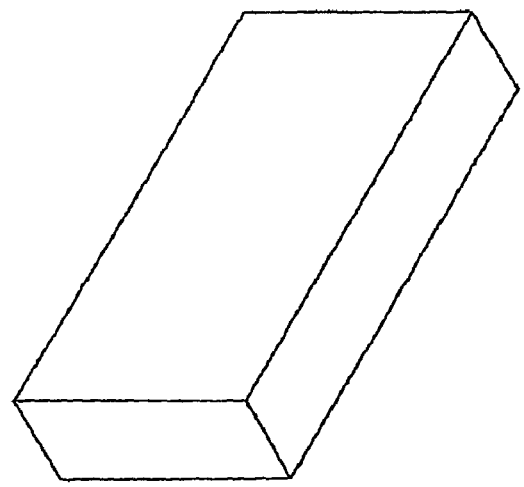
FIG. 27

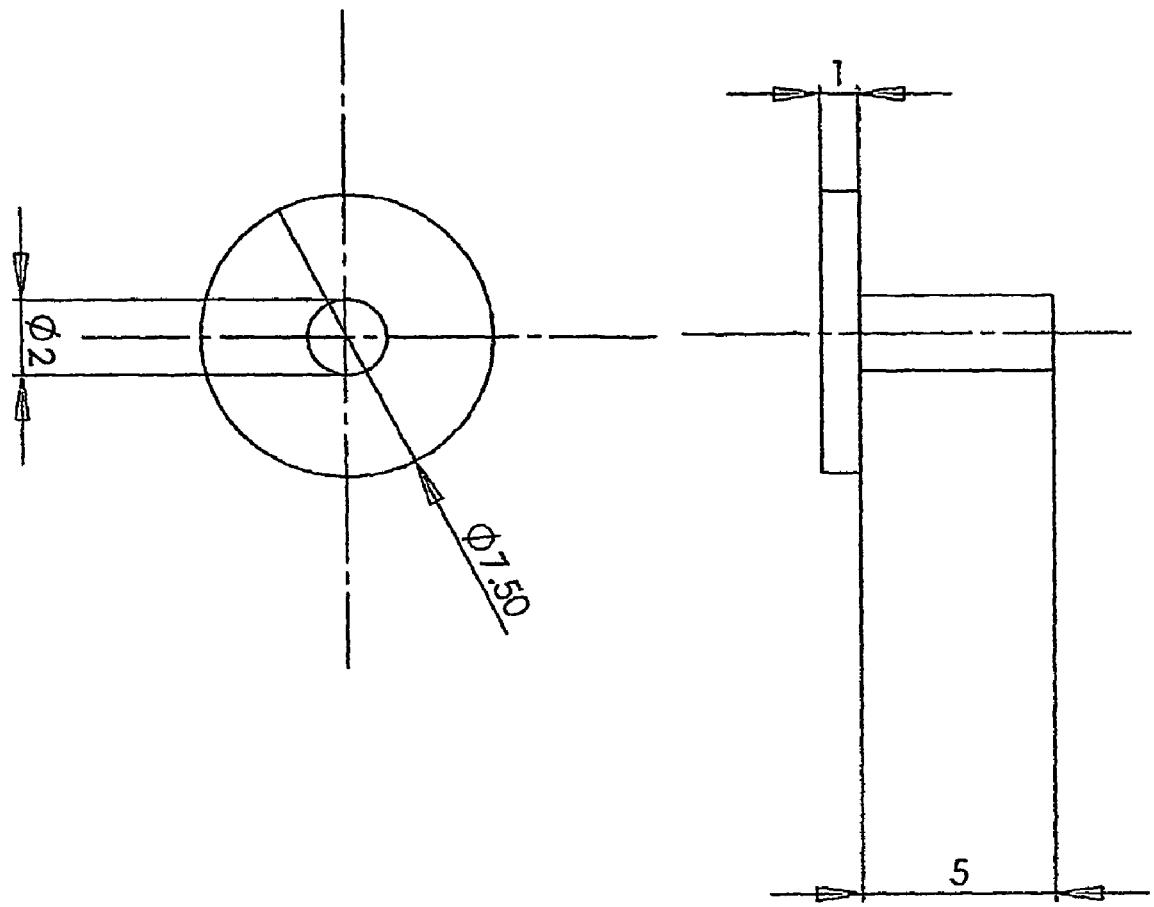
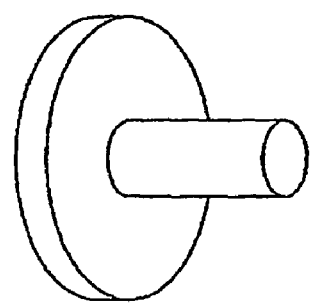
FIG. 28

CERVICAL COLLAR

FIELD OF THE INVENTION

The present invention generally relates to a collar, i.e., a cervical collar adapted to airway maintenance with cervical spin control. More specifically, the present invention relates to a jaw thrusting cervical collar adapted to maintain airway device introduce to the patient at the very first step of trauma treatment.

BACKGROUND OF THE INVENTION

The human spine comprises some vertebrae grouped into three sections according to location: cervical spine (neck), thoracic spine (middle back), and lumbar spine (lower back). Soft tissues, including ligaments, muscles, and skin, surround and support the spine. Seven of the vertebrae form the cervical spine connecting the base of the head to the thorax (trunk and shoulders) and supporting the head.

In the practice of emergency medicine and the treatment of trauma, when damage to the cervical spine in suspected, there is often a need to secure the head and neck of a patient, to prevent movement of the cervical spine vertebrate and deterioration of the patient's condition. Spinal cord damage can result in partial or complete paralysis or even death.

Cervical collars are a common protective device well known in the medical art. In the treatment of spinal cord damage it is common to perform x-ray or similar imaging of the damaged area. Therefore cervical collars are often made of materials transparent to x-rays. Cervical collars are additionally often required to be lightweight and comfortable, and also to be cheap and easy to manufacture.

Furthermore, in the practice of emergency medicine and the treatment of trauma it is common for a patient to loose consciousness and the ability to maintain open airways and respiration. Loss of respiration is often fatal. There are several methods known in the art for maintaining open airways. One invasive technique is surgical cricothyroidotomy involving the insertion of a tube through the neck of the patient.

There is therefore a need simultaneously to protect the spine and maintain open airways, as both conditions, damage to the spine and suffocation, are highly damaging, often fatal, and usually irreversible. Therefore there is a need for cervical collars to enable opening of the airways. It is thus common for cervical collars to comprise a hole or an opening in the region of the front of the neck to allow invasive techniques such as surgical cricothyroidotomy.

There are techniques known in the art for maintaining open airways by maintaining an open mouth. Being less invasive than perforating the neck, they are usually preferable. However, the need to open the mouth of a patient tends to conflict with the requirement of maintaining a rigid position of the head to prevent damage to the spine. There are techniques known in the art for opening the mouth while minimizing other motion of the head. Such techniques include several variations on the jaw thrust maneuver. Existing cervical collars tend to interfere with the execution of such techniques, and none assist such non-invasive techniques.

The following is a list of variations of cervical collars and similar devices. Some describe means for enabling circulation of air around the neck, some comprise a hole or an opening in the region of the of the neck, but none describe means for opening the mouth in order to maintain open airways into the lungs.

Various patent show means for immobilizing the head of injured patients. Hence, U.S. Pat. No. 5,048,509 to Grundei et al. discloses a cervical support that has an inherently stable support body of elastic foam material, and a jaw support regions which extend symmetrically and in mirror image relationship with respect to an imaginary longitudinal axis connecting the centers of the nape support region and the chin support region. This collar constructed from two parts adapted to be mutually assembled rigidly, without effective means of maneuvering mandibular-clasping members of the collar. Similarly, U.S. Pat. No. 5,785,058 to Reynolds teaches a disposable head and neck immobilization device allows reducing contamination hazard from transfer of bodily fluids. The mandibular is effectively fastened by means of said collar, yet airway maintenance is not provided.

Lastly, U.S. Pat. No. 5,682,632 to Cotroneo presents a head rest device for use under a patient's head, the device comprising a base and a jaw thrust support having at least two protuberances extending upward from the upper surface of the base for engaging with the patient's mandible at angles of the mandible so that the patient's mandible is thrust out distracting the patients tongue and associated structures in a direction away from the patients head and neck, and in so doing, opening the patient's oropharynx and hypopharynx and lifting the patients epiglottis out from in front of the patient's laryngeal inlet. A portable cervical collar adapted to providing trauma patient treated in the field and transferred to hospital an airway maintenance with cervical spin control is yet not available and thus meets a long felt need.

SUMMARY OF THE INVENTION

It is thus the core of the present invention to provide a medical device that simultaneously performs two conflicting functions, the first function is to protect the neck by restricting the movement of the head against the rest of the body, and the second function is to prevent suffocation by maintaining an open path by which air may flow to the lungs in the least invasive way possible.

It is hence in the scope of the present invention a cost effective cervical collar useful for maintaining the airways in head and neck immobilized trauma patient open. Said collar comprising inter alia a rigid motion-restricting frame attached to the head; and a jaw clasp attached to the jaw. Its novelty is generally characterized by that it is simultaneously restricting the motion of the head and neck while allowing motion of the jaw to maintain open airways.

It is further in the scope of the present invention wherein the aforementioned collar additionally comprising a restrictor member restricting the motion or location of the jaw clasp relative to the rigid frame; and/or wherein the restrictor limits the distance between the rigid frame and the jaw clasp and/or wherein the restrictor limits the direction of motion between the rigid frame and the jaw clasp.

It is further in the scope of the present invention wherein the aforementioned collar additionally comprising a lock member preventing the motion of the jaw clasp relative to the rigid frame.

It is another object of the present invention to present a jaw clasp, generally useful for performing the jaw-thrust maneuver motion of the jaw to maintain open airways. This novel collar comprising a plurality of n movable fitting elements adapted to fit the jaw tightly; and a plurality of n movable mover elements adapted to move the jaw, wherein n is an integer number between 1 to 8, preferably 2 or 4. Alternatively or additionally, the jaw clasp may comprise a cervical collar adapted to immobilized head and neck of trauma patients. Additionally, the collar may comprise a restrictor resting the motion or location of the mover elements relative to the cervical collar and/or a lock member preventing the motion of the mover elements relative to the cervical collar. Preferably, the restrictor may limit the distance between the fitting elements and the cervical collar, and/or the direction of motion between the fitting elements and the cervical collar.

It is lastly another object of the present invention to present a useful method for performing the jaw-thrust maneuver wherein the patient is immobilized with a cervical collar, wherein the jaw of the patient is fitted with a clasp and further wherein the clasp is allowed to move along a restricted path. Said method comprising the following steps:

fitting the patient with a cervical collar,
fitting the patient with a jaw clasp;
using the jaw clasp to perform the jaw-thrust maneuver, and wherein the step of fitting the cervical collar comprises steps of fitting various parts of which the cervical collar is assembled.

BRIEF DESCRIPTION OF THE INVENTION

Figure 2:
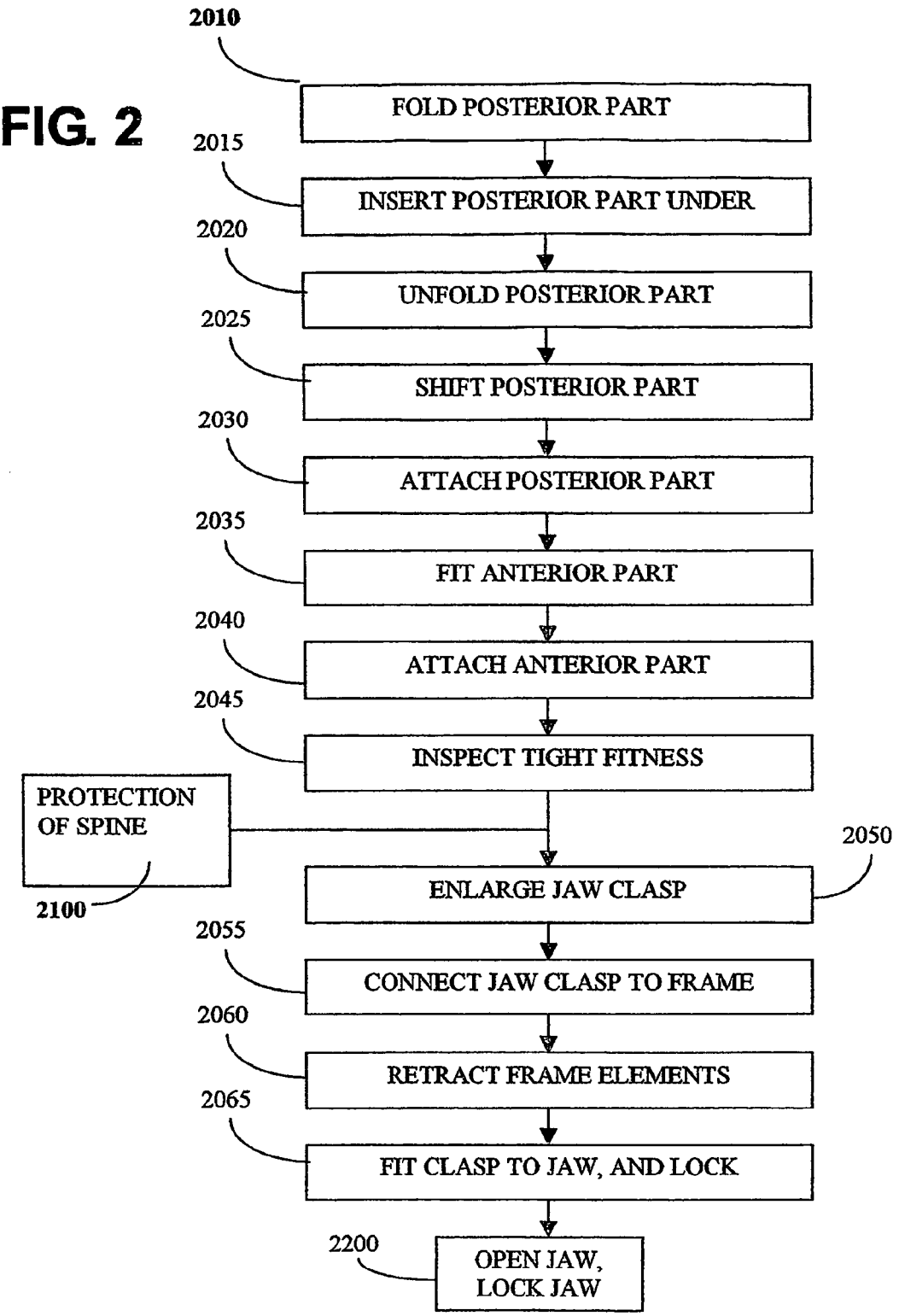
Figure 3:
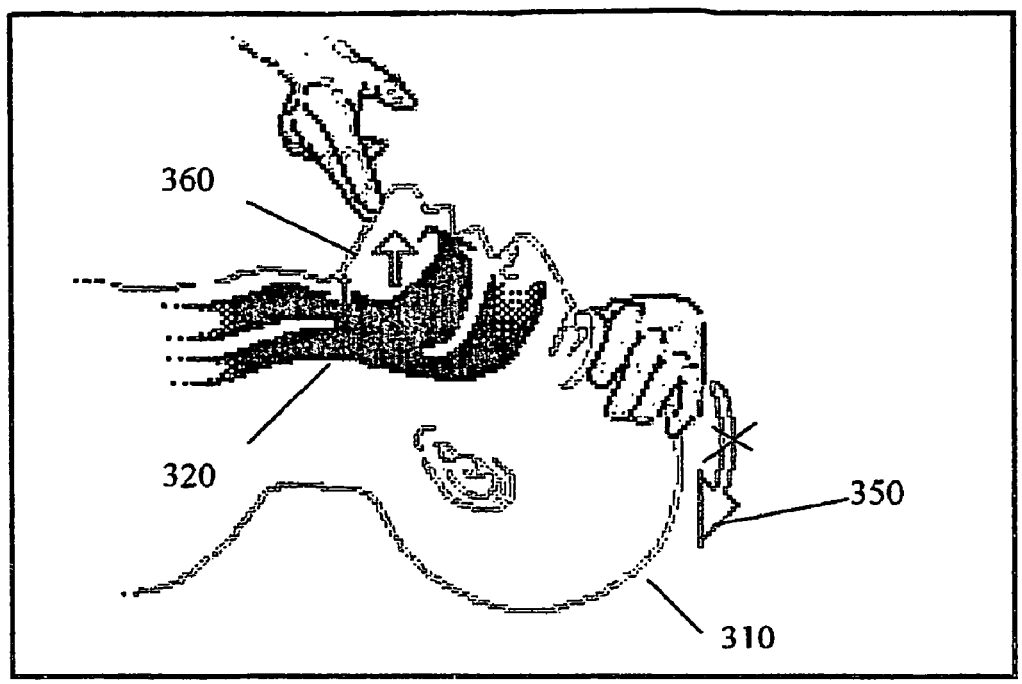
Figure 4:
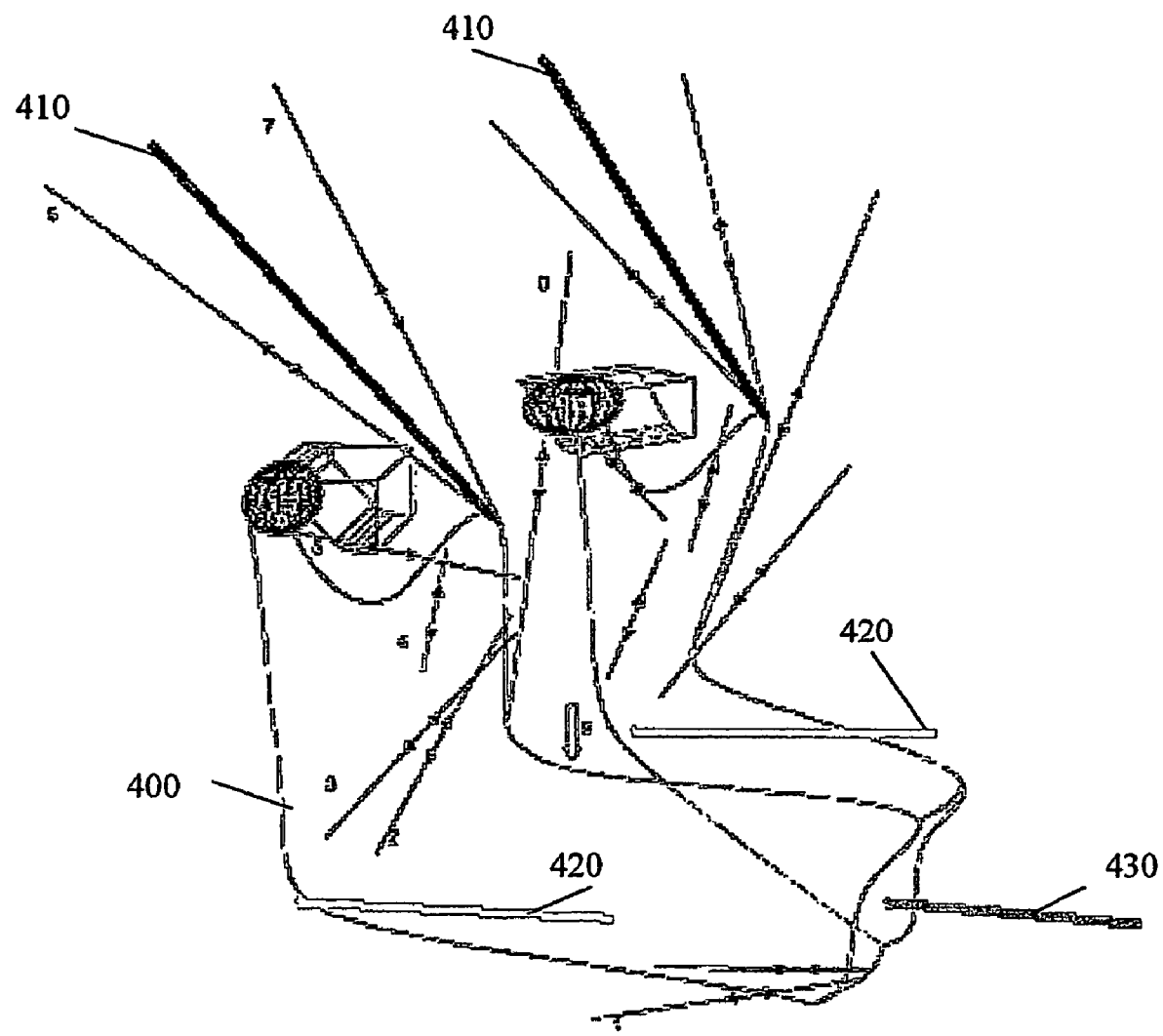
Figure 5:
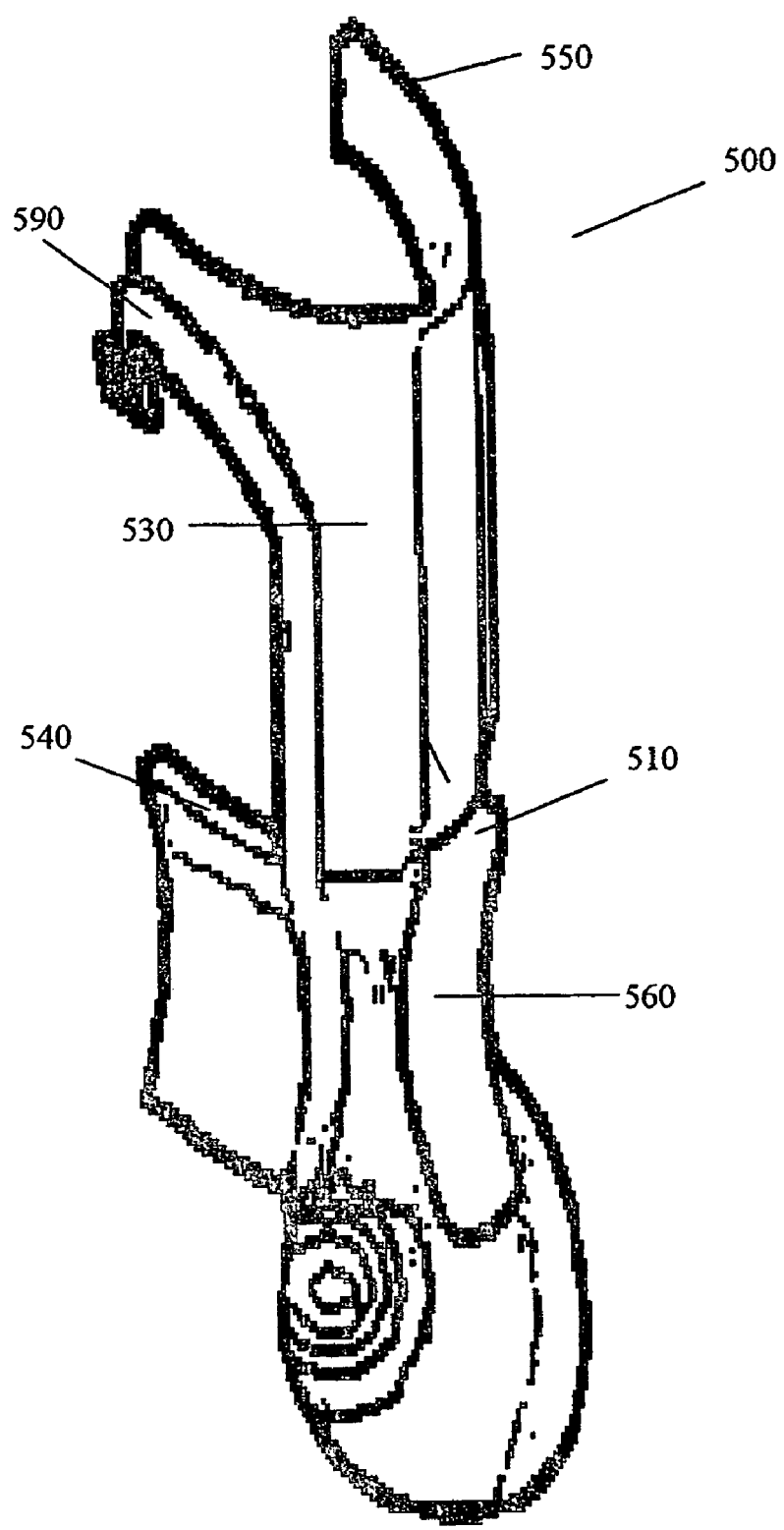
Figure 6:
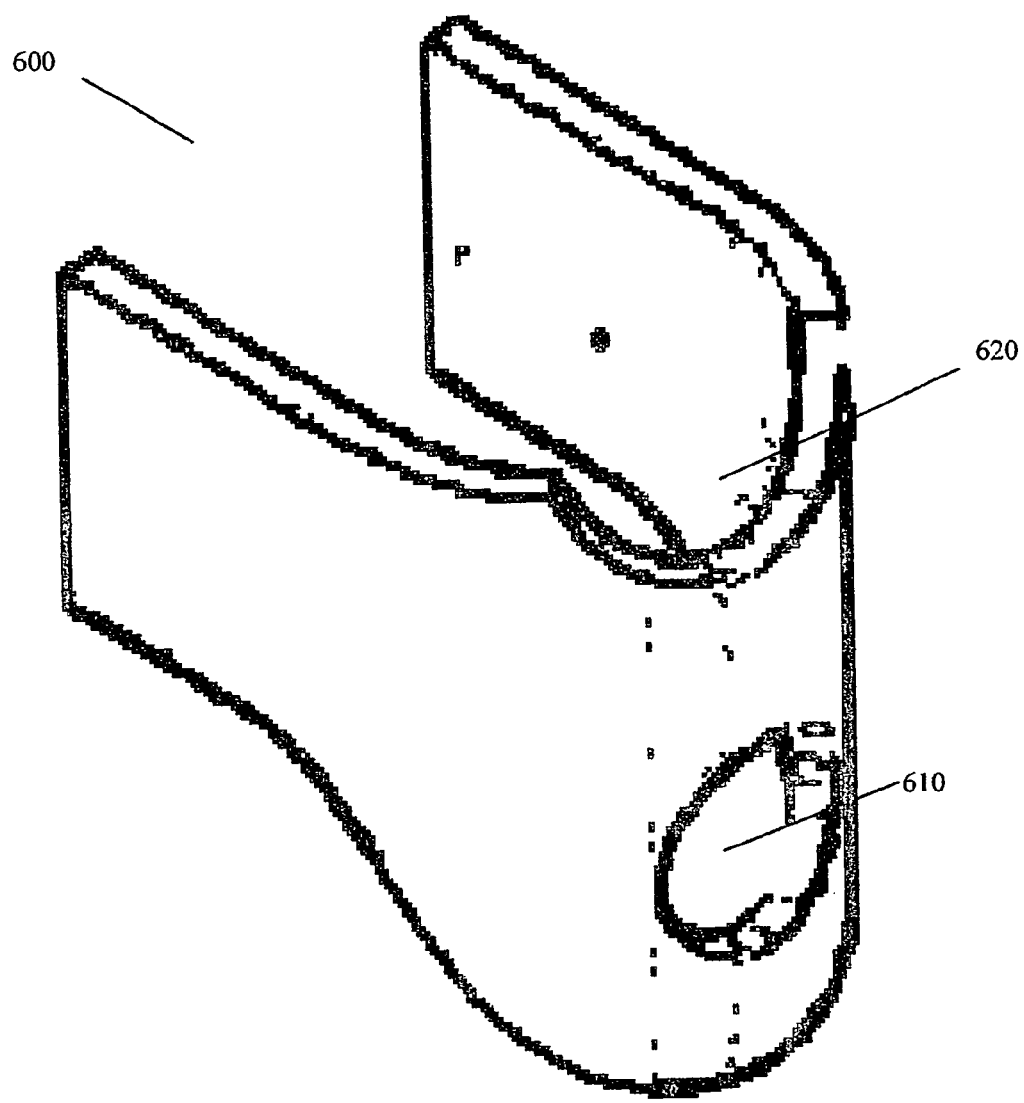
Figure 7:
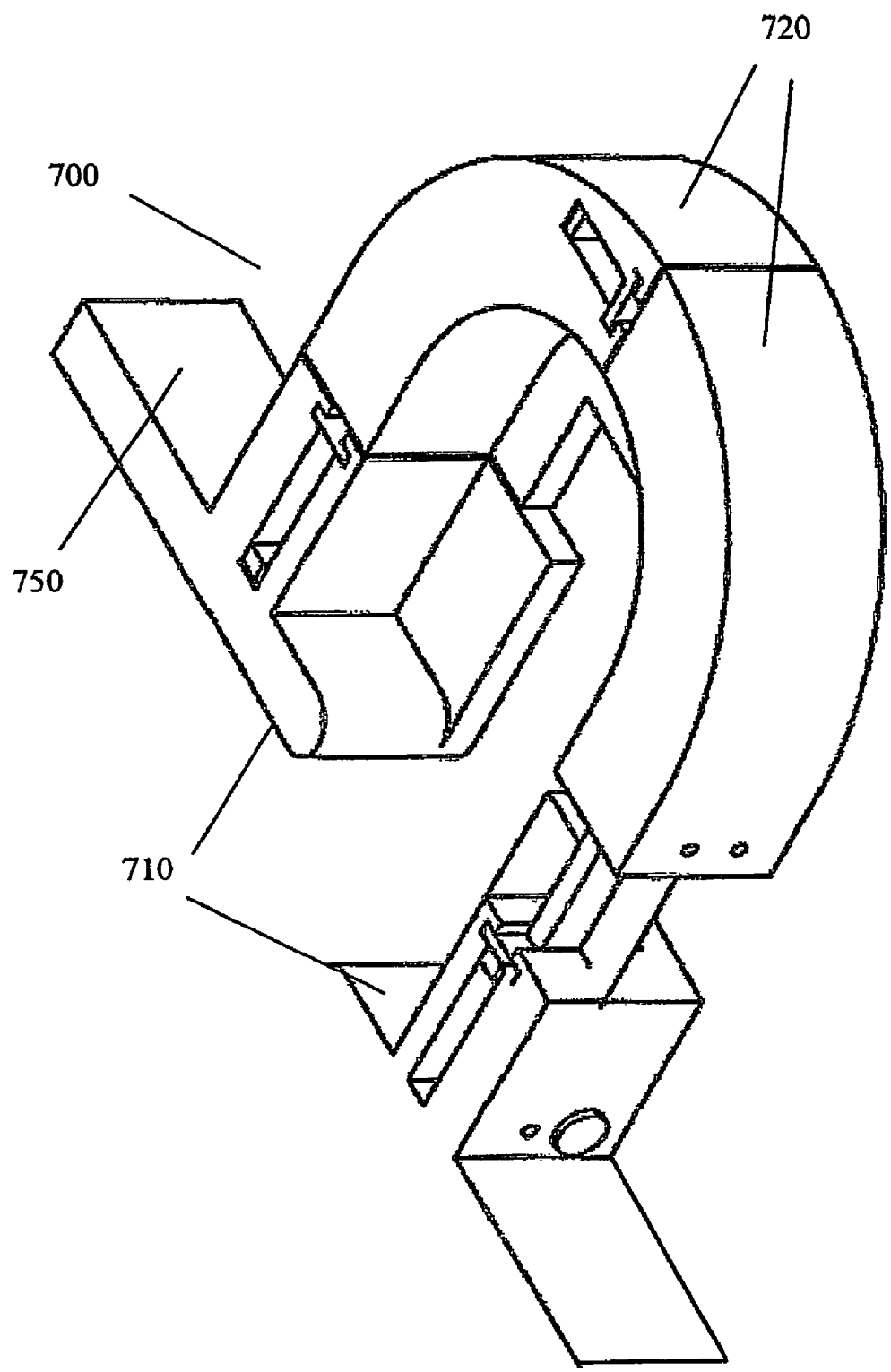
Figure 8A:
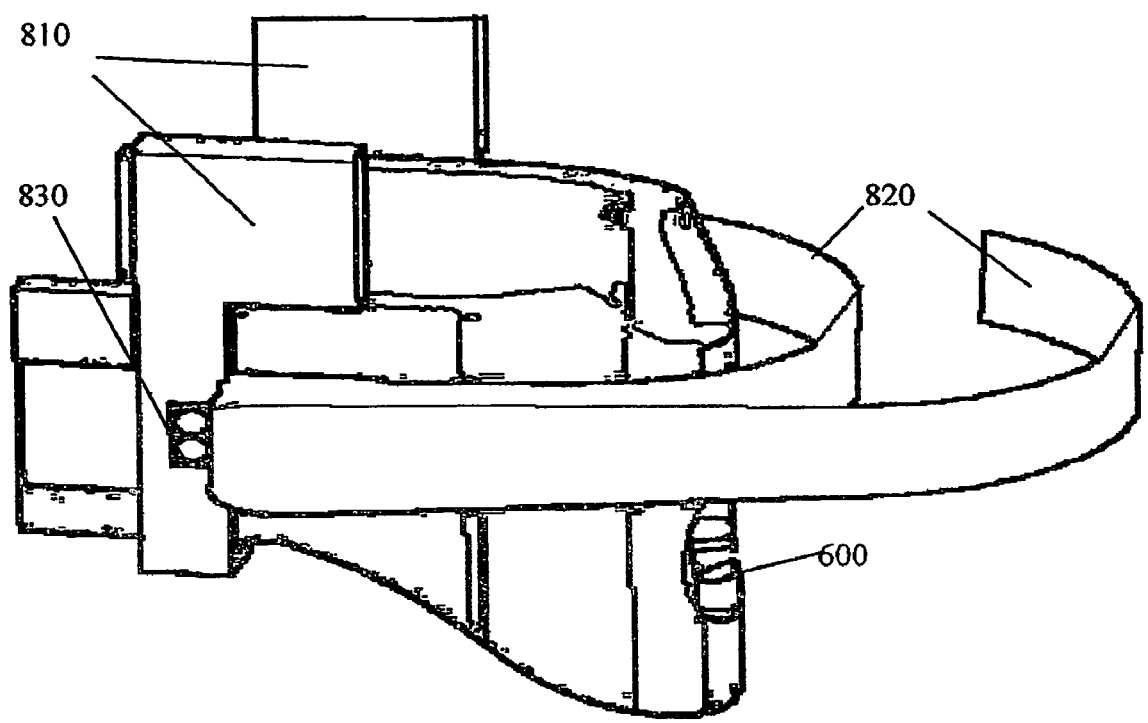
Figure 8B:
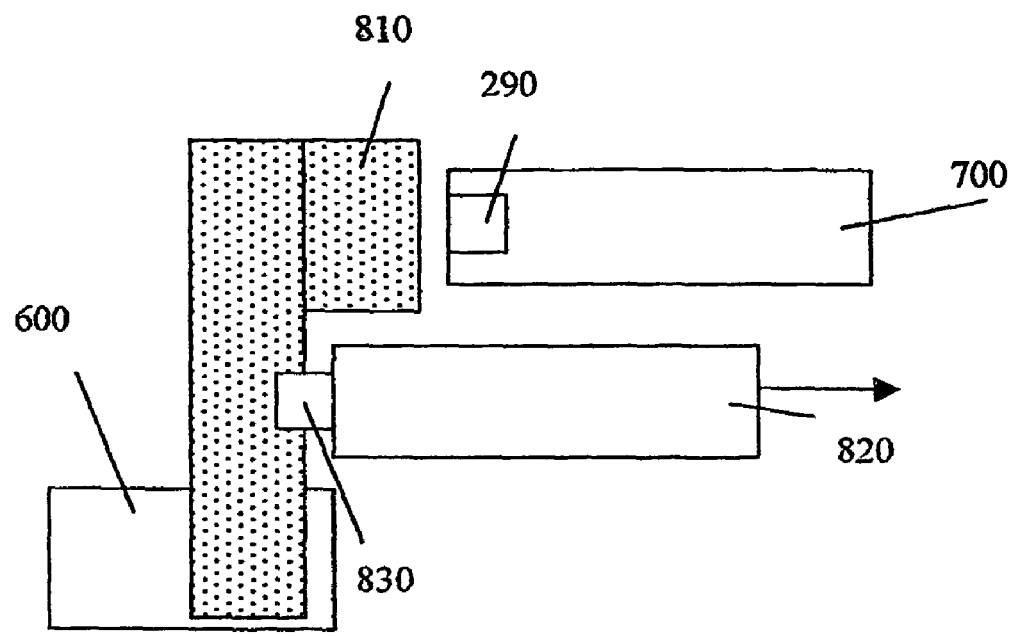
Figure 9:
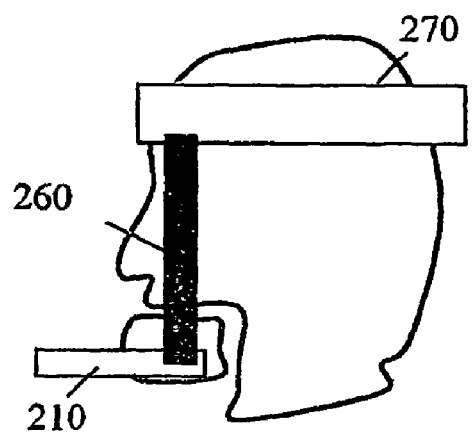
Figure 10B:
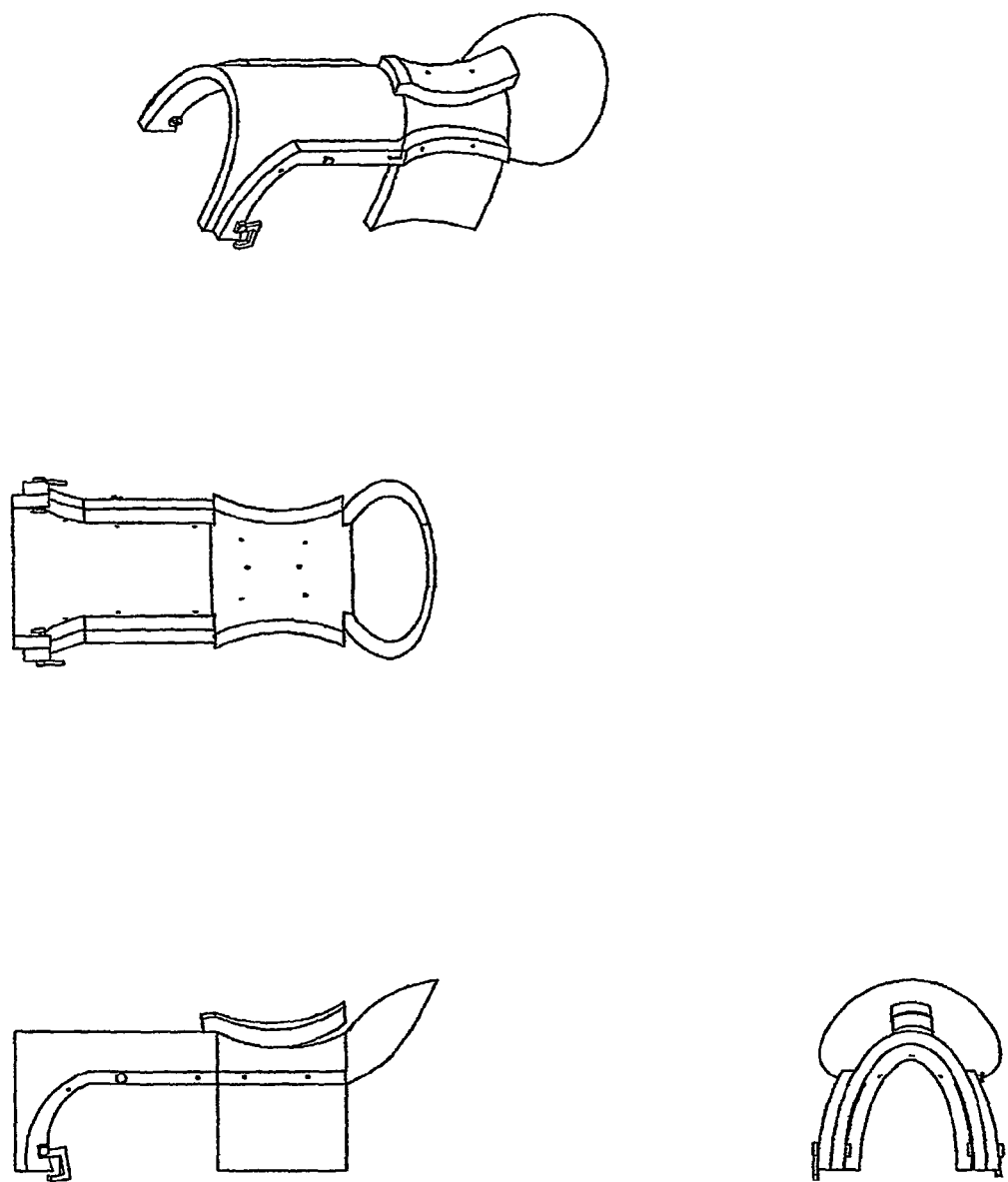
Figure 11:
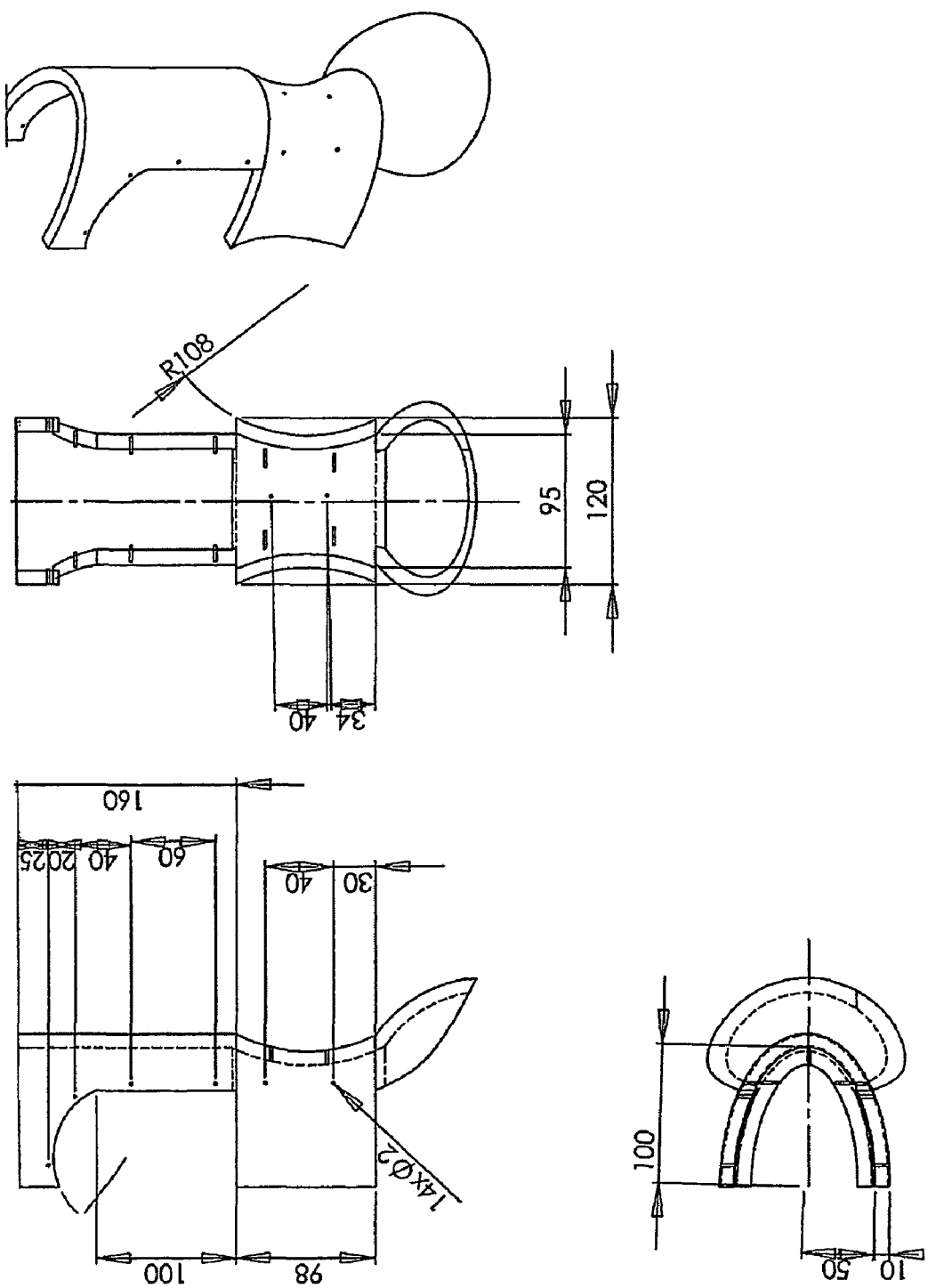
Figure 13:
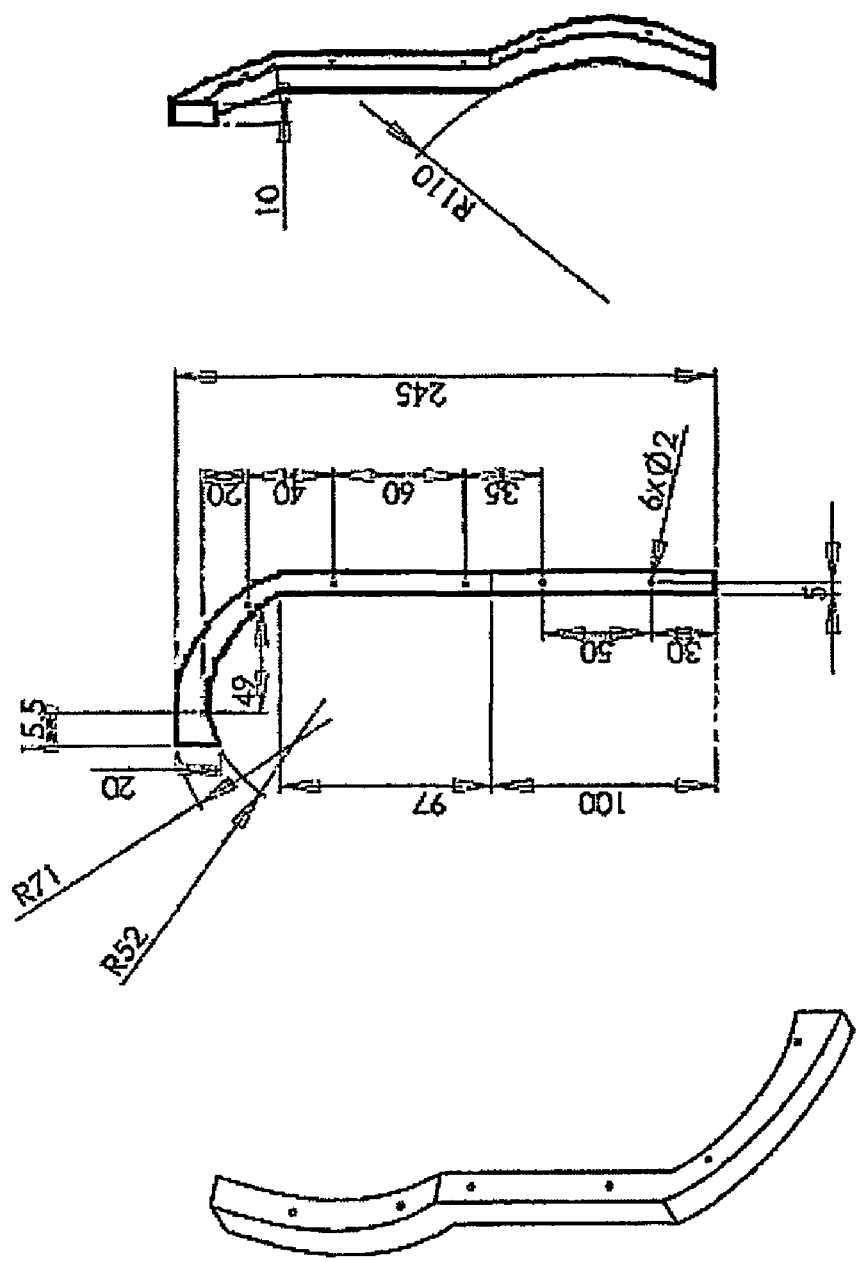
Figure 15:
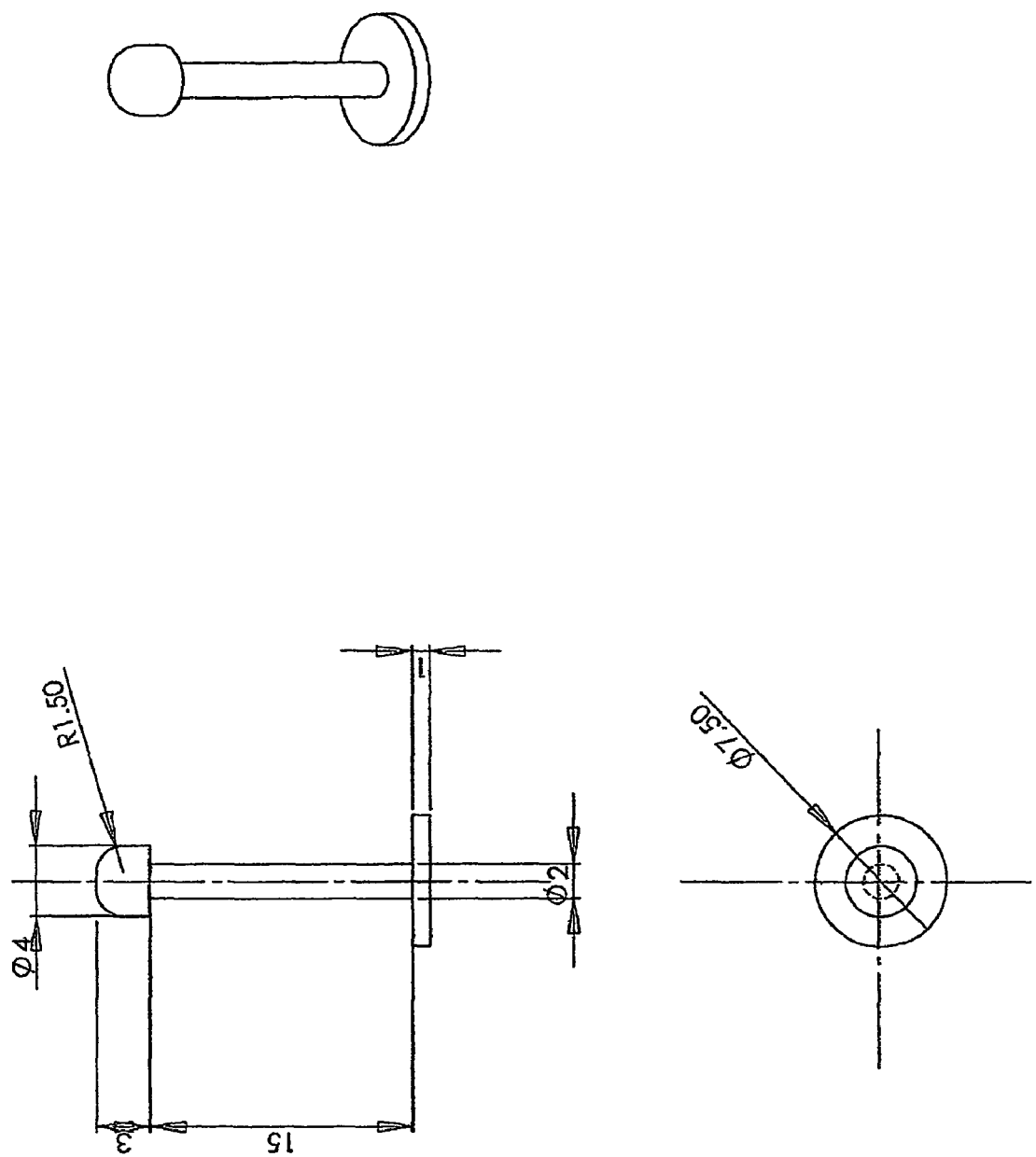
Figure 16:
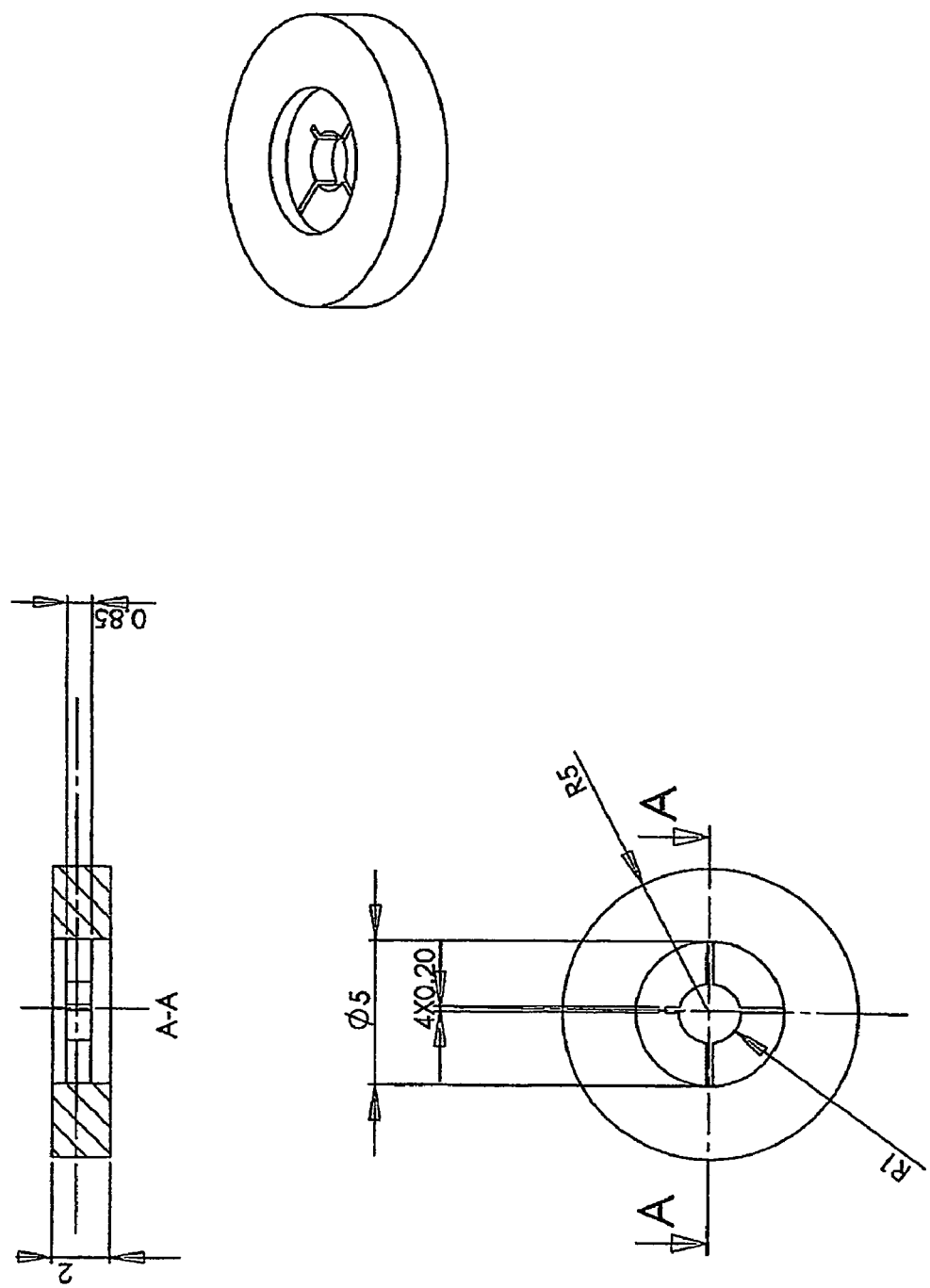
Figure 17:
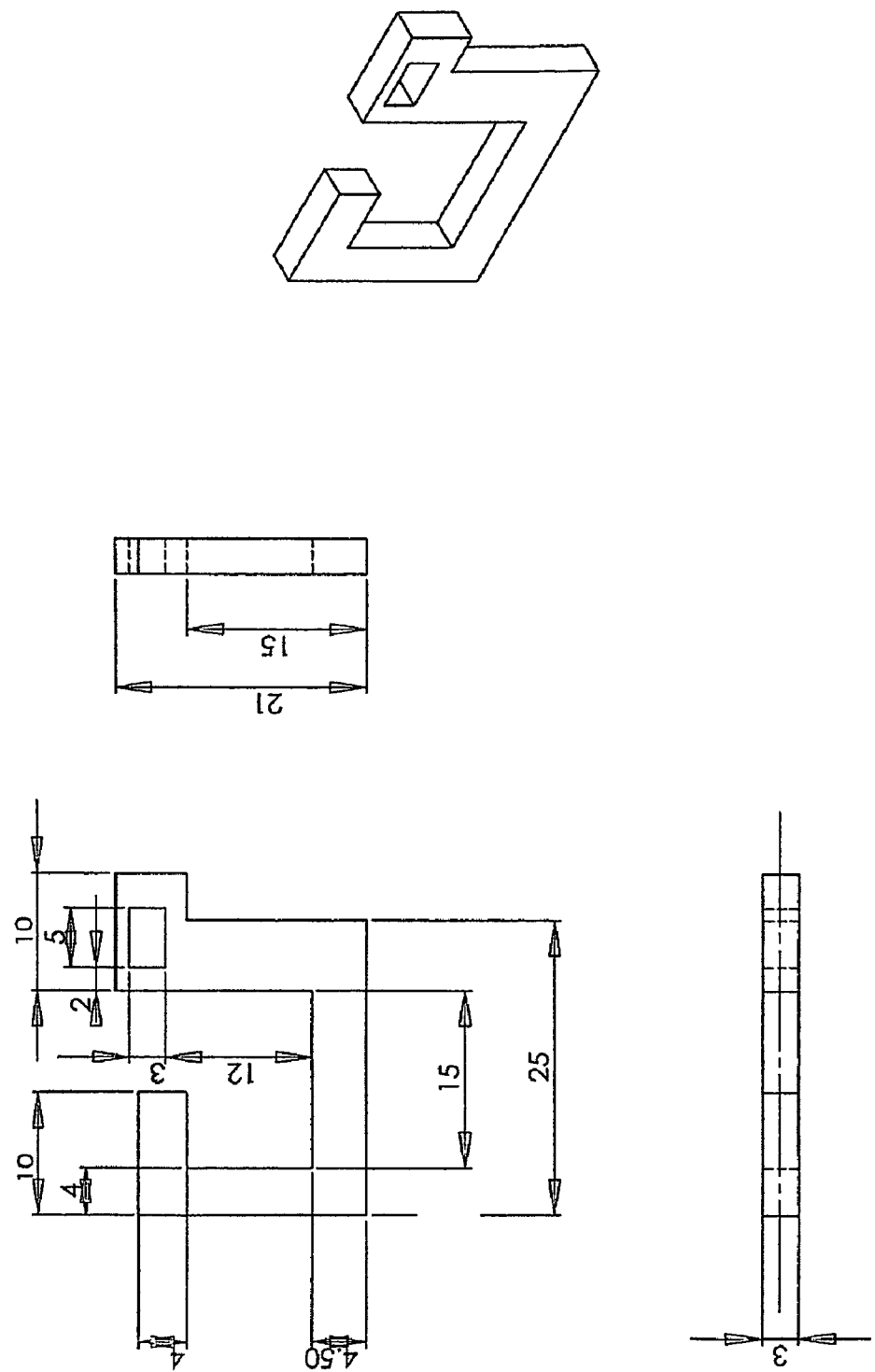
Figure 22A:
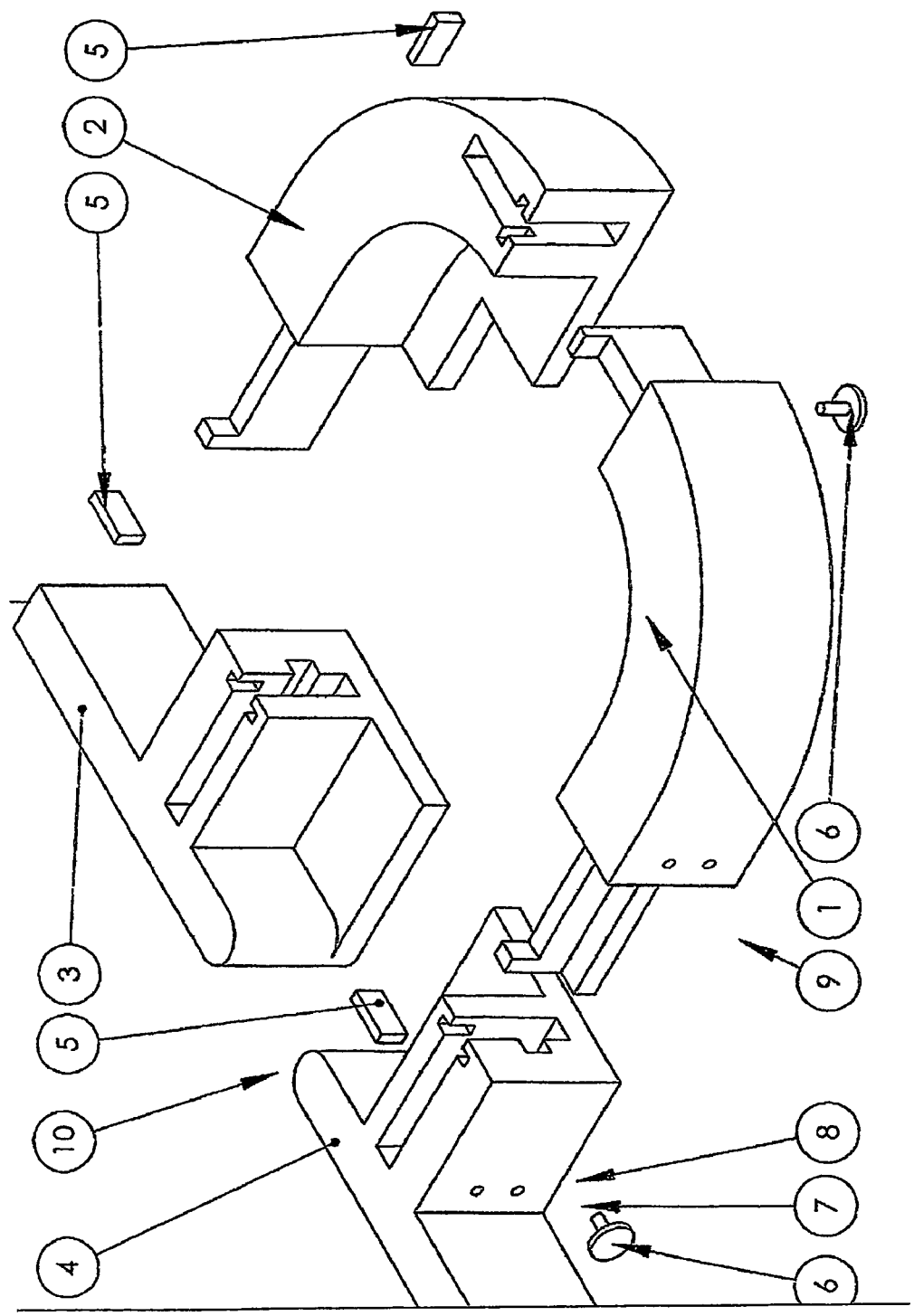
Figure 29:
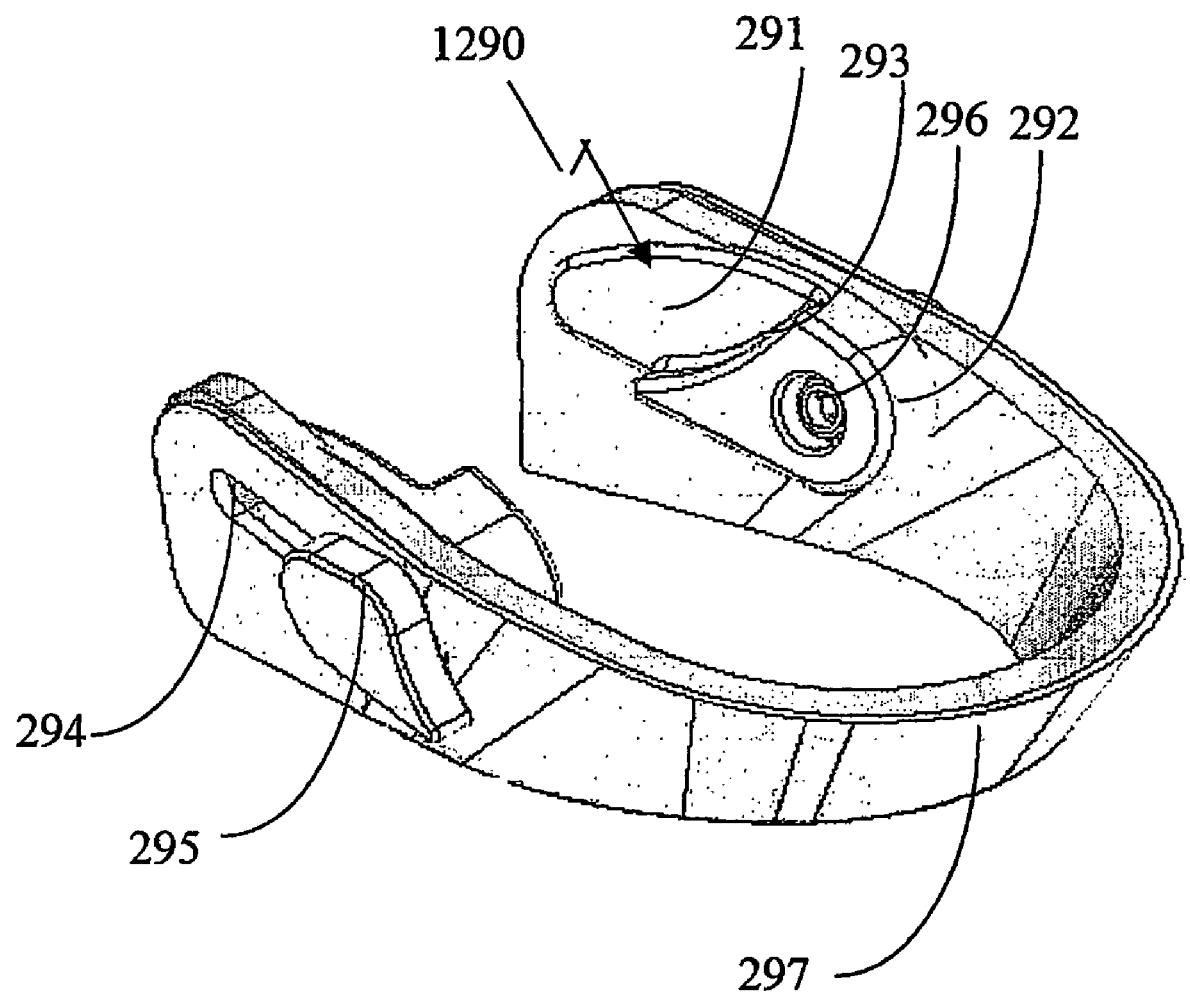
Figure 30:
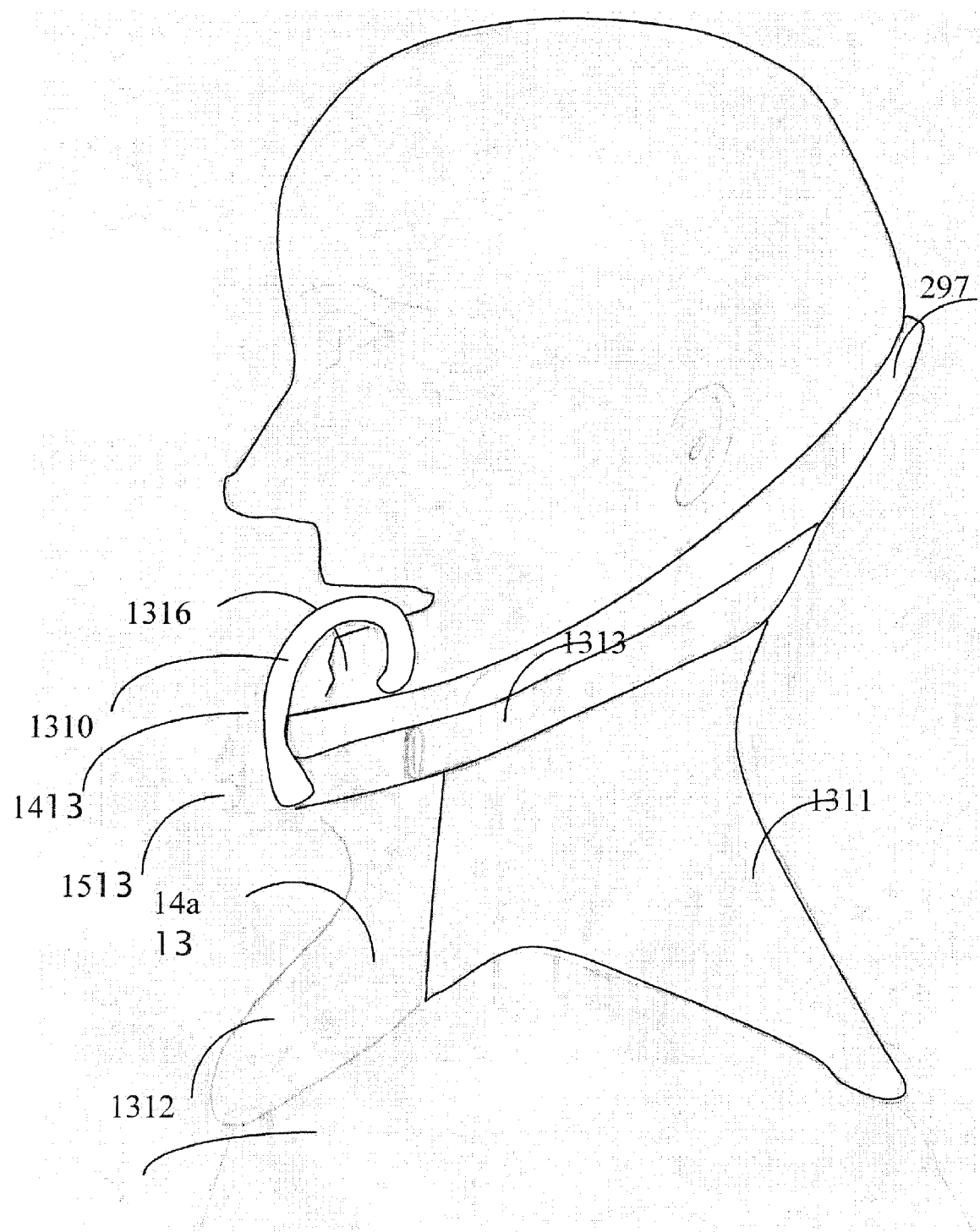
Figure 31:
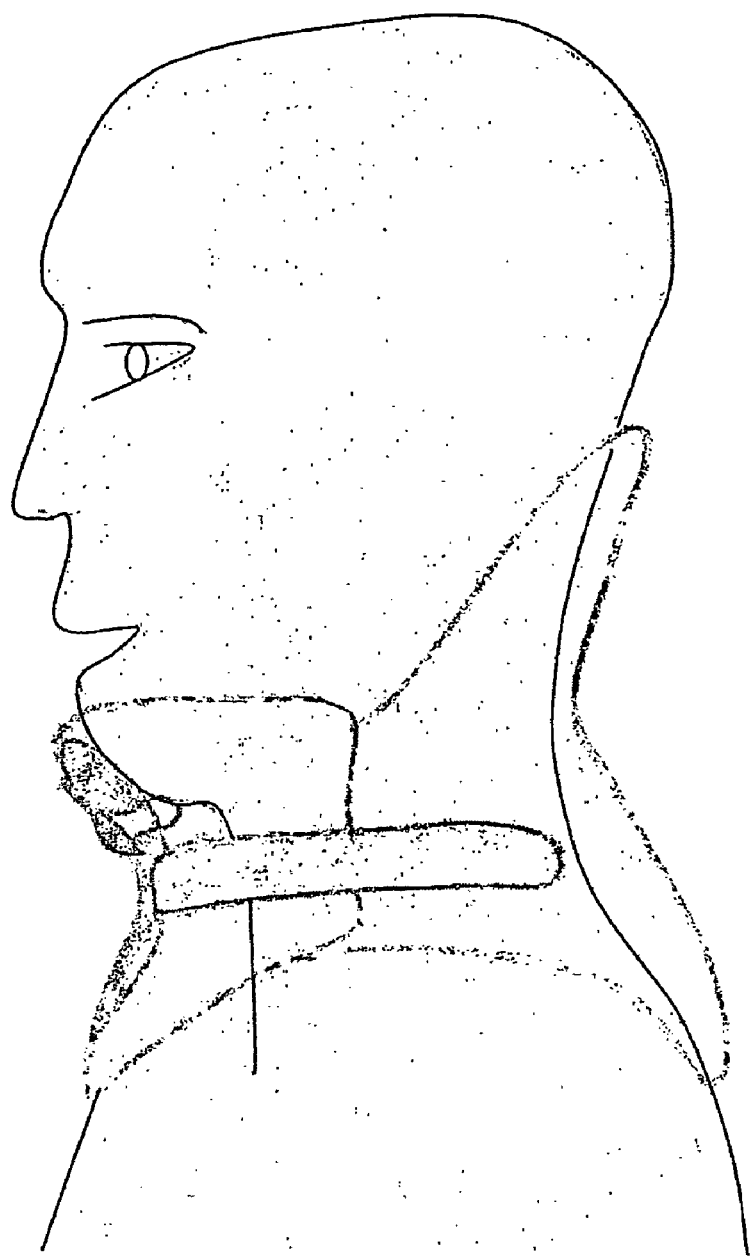
Figure 32:
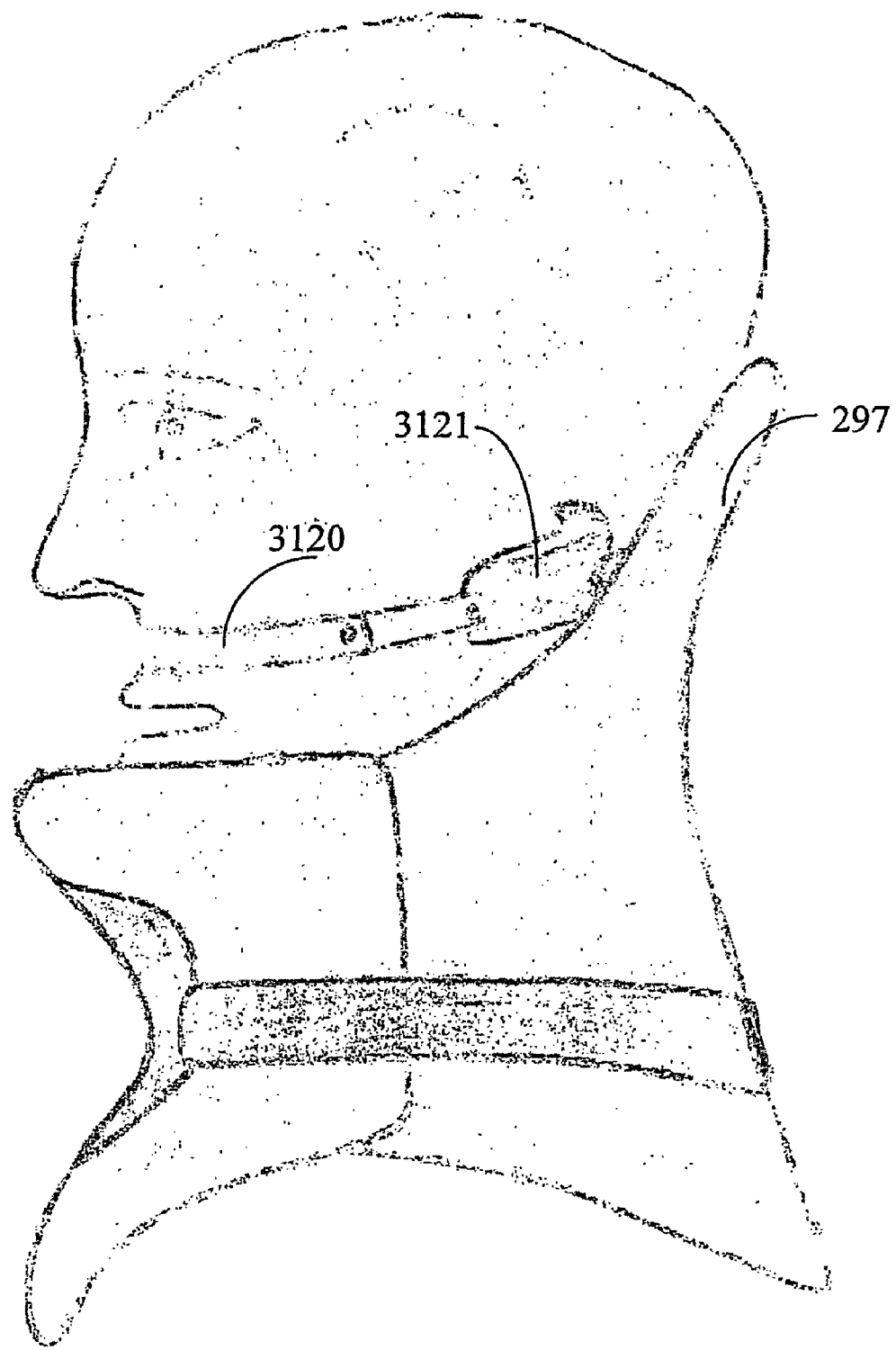

In order to understand the invention and to see how it may be implemented in practice, a plurality of embodiments will now be described, by way of non-limiting example only, with reference to the accompanying drawings, typical dimensions are sometimes appended to the drawing as an example only, such that those who are skilled in the art may understand the described embodiment better:

FIG. 1 schematically presents major components of the present invention by function rather than by form; it depicts the function of major components in relation to the head of a patient, rather than their preferred shape and exact location in relation to the head; the head is depicted as composed of two units: the jaw 110, and the rest of the head 100; the component of the present invention whose function is to attach to the jaw is depicted as block 210; the component of the present invention whose function is to aid in moving block 210 and thus jaw 110 is depicted as block 290; the components of the present invention whose function is to control and direct the (-forward) movement of blocks 210 and 290 are depicted as the lock member block 250 in FIG. 1 and the restriction member block 260 in FIG. 1; block 240 describes the attachment of block 250 and block 260 to rigid block 230; the function of the other blocks 220, 230, 240, 270 and 280 is to attach to the head (blocks 270 and 280) e.g., by a means of a strip, compose a rigid structure (block 230), and control the motion of the head in relation to the rest of the body of the patient (block 220);

FIG. 2 describes a preferred procedure for the use of a preferred embodiment of the present invention, an embodiment comprising essentially 3 parts;

FIG. 3 schematically presents a situation in which the present invention is of practical use; a patient is depicted by head 310, jaw 360 and airways 320; the patient is depicted as being handled in order to open airways 320, and in particular head 310 is depicted as being undesirably moved along arrow 350, and the jaw is being lifted;

FIG. 4 schematically presents the forces applied on a jaw (400) as it is being forced open against resistance of the muscles; various arrows depict the direction of forces extracted by various muscles, the sum of which is depicted by a pair of lines 410; an external pair of forces directed to open the jaw in attachment to its two sides is two sides is depicted as a pair of lines 420, and a single force directed to open the jaw in attachment to the chin is depicted as line 430;

FIG. 5 schematically presents a structural part of a preferred embodiment of the present invention marked as part 500; part 500 is designed to be located at the back of the head of the patient, and to attach to the head; it comprises rigid parts (510 and 530), soft parts and attachment components: attachment to head 550, attachment to front 540, attachment to jaw related parts 590, and attachment to the rest of the body of the patient, 560;

FIG. 6 schematically presents a structural part of a preferred embodiment of the present invention marked as part 600; part 600 is designed to be located at the front of the neck of the patient, and to support to the head, while allowing the airways to be opened by use of hole 610 and groove 620;

FIG. 7 schematically presents a structural part of a preferred embodiment of the present invention marked as part 700; part 700 is designed to be attached to the jaw in a fitting fashion; it comprises parts that can move in relation to each other and then lock in position; parts 710 (left and right) fit the back of the jaw, and parts 720 (left and right) fit the front of the jaw;

FIG. 8A, FIG. 8B and FIG. 8B schematically present some structural parts of a preferred embodiment of the present invention involved in the movement of the jaw; strap or straps 820 move the pair of elements 810 forward through connecting element 830;

FIG. 9 schematically presents an element of a preferred embodiment providing the function of limiting the location of other moving elements; it is denoted as the restriction member block 260 in the figure;

FIGS. 10A, 10B, 10C, 11, etc. through FIG. 28 are a set of detailed technical drawings instructing a person skilled in the art how to manufacture a preferred embodiment of the present invention;

FIGS. 10A, 10B, 10C, 11, etc. through FIG. 17 provide a detailed disclosure of the part labeled as 500 in reference to FIG. 5;

FIG. 10A schematically presents the assembly of part 500;
FIG. 10B schematically presents part 500 when fully assembled;
FIG. 10C comprises a table listing various elements of part 500 and disclosing their quantities;
FIG. 11 schematically presents part 500 along with its preferred dimensions;
FIGS. 12 and 13 details a pair of elements of part 500 that is collectively labeled 530;
FIG. 14 schematically presents an element of part 500 that is labeled 510;
FIG. 15 schematically presents a pin;
FIG. 16 schematically presents a nut;
FIG. 17 schematically presents a hook;
FIGS. 18A, 18B, 18C, 19, 20 and 21 provide a detailed disclosure of elements described in reference to FIGS. 8A, 8B and 8C;
FIG. 18A schematically presents the assembly of elements around part 600;
FIG. 18B schematically presents the same elements when fully assembled;
FIG. 18C comprises a table listing various elements and disclosing their quantities;
FIG. 19 schematically presents part 600 along with its dimensions;
FIGS. 20 and 21 details a pair of elements that are collectively labeled 810;
FIGS. 22A, 22B, 22C, 23A, 23B, 24A, 24B, 25A, 25B, 26A, 26B, 27 and 28 provide a schematically detailed disclosure of part 700 described in reference to FIG. 7.
FIG. 22A schematically presents the assembly of part 700;
FIG. 22B schematically presents the same elements when fully assembled;

FIG. 22C comprises a table listing various elements and disclosing their quantities;

FIGS. 23A, 23B, 24A and 24B schematically presents a pair of elements collectively labeled 720;

FIGS. 25A, 25B, 26A and 26B schematically presents a pair of elements that are collectively labeled 710;

FIG. 27 schematically presents an element for a locking rail;

FIG. 28 schematically presents a nail;

FIG. 29 schematically presents cervical collar comprising a 'jaw thrust'-like knob according to one embodiment of the present invention, FIG. 30 schematically presents 'Chin lift' collar according to one embodiment of the present invention;

FIG. 31 schematically details both lifted chin conformation of lever and its un-lifted chin conformation; and, FIG. 32 schematically presents another embodiment of the present invention, wherein a maxillary support is provided.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the general principles of the present invention have been defined specifically to provide protection to the neck by restricting the movement of the head against the rest of the body, and simultaneously to provide means of maintaining an open path through which air may flow to the lungs.

The term 'airway' refers in the present invention to any passage for a current of air into or out of the lungs.

The term 'collar' refers in the present invention to any device comprised of parts wrapped around the neck.

The term 'jaw-thrust maneuver' refers in the present invention to a technique to open an airway by placing fingers behind the angle of a jaw of a patient, usually fingers of one hand on each side, and displacing the mandible forward; said technique is usually used when said patient may have a cervical spine injury. The same term is also used in the present invention to the same technique applied by mechanical devices rather than fingers.

Terms relating to direction, such as 'up' and 'forward' refer in the present invention to directions defined herein below in reference to FIG. 2.

The term 'ABS' specifically refers in the present invention to a plastic material named Acrylonitrile Butadiene Styrene, yet more generally related to any thermoplastic polymer composition, adapted to be molded easily and cost-effectively.

The airway marinating cervical collar according to the most general embodiment of the present invention, is schematically characterized by a rigid frame protecting the head and neck, while restricting their relative motion one against the other, and simultaneously providing means to prevent suffocation by maintaining the patient's airways open by enabling the movement of the jaw.

According to one embodiment of the present invention, the enabled movement of the jaw is essentially in the forward direction, and to a minor extent in a downward direction, as is normally the case in the jaw-thrust maneuver.

According to another embodiment of the present invention the enabled movement of the jaw is both in the forward direction and in a downward direction.

According to yet another embodiment of the present invention the position of the jaw can be fixed when the jaw is located in a desired position.

According to one embodiment of the present invention a rigid structure is formed essentially of one collar wrapped around the head and neck.

According to another embodiment of the present invention a rigid structure is formed essentially of several parts connected together to fit a specific patient.

According to one embodiment of the present invention a rigid structure is formed by avoiding any holes or dents in its form that are not essential.

According to another embodiment of the present invention holes or dents allow access to the ears of the patient.

According to another embodiment of the present a invention holes or dents allow access to the front of the neck of the patient.

Reference is now made to FIG. 1, presenting a schematic and generalized presentation of the aforementioned novel airway maintaining cervical collar 50.

FIG. 1 schematically presents major components of the present invention by function rather than by form. It depicts the function of major components in relation to the head of a patient, rather than their preferred shape and exact location in relation to the head. The head is depicted as composed of two units: the jaw 110, and the rest of the head 100. The present invention provides the benefit of allowing jaw 110 to move in relation to head 100. This movement is preferably in a forward and slightly downwards direction. By allowing this motion the present invention allows an open airway to be maintained through the open mouth and to the lungs. The component of the present invention whose function is to attach to the jaw is schematically depicted as block 210. Details of how this function is provided are disclosed, inter alia, in reference to FIG. 7. The component of the present invention whose function is to aid in moving block 210 and thus cause the movement of jaw 110 is schematically depicted as block 290. Details of how this function is provided are disclosed, inter alia, in reference to FIG. 7 and FIG. 8A. The components of the present invention whose function is to control and direct the movement of blocks 210 and 290 are schematically depicted as the lock member block 250 in FIG. 1 and the restriction member block 260 in FIG. 1. Block 250 directs the movement relative to head 100 and also prevents motion when it is not desired, usually when the jaw is already positioned in the desired position relative to the head, usually when it is open and allowing the passage of air. Details of how this function is provided are disclosed, inter alia, in reference to FIG. 8A, FIG. 8B, and FIG. 8C. Block 260 prevents block 210 from wandering too far from the rest of the parts of the present invention, as may happen at times when block 210 is not attached the jaw. It is acknowledged in this respect that optional block 260 may be constructed as a rubber strip, adapted to be attached at the right and/or left side of the collar, and is especially adapted to support block 210. Details of how this function is provided are disclosed, inter alia, in reference to FIG. 9. Block 240 performs the function of attaching block 250 and block 260 to rigid block 230. Details of how this function is provided are disclosed, inter alia, in reference to FIG. 5. Blocks 270 and 280 perform the function of attachment to the head 100. Two blocks are schematically depicted to show that the attachment can be made at one or more locations.

Attachment to the head is limited in form, composition and location by many considerations including the following:

the jaw should be kept free to move,
the mouth should not be blocked, the nose should not be blocked,
the ears should not be blocked to sound or for diagnosing presence of either blood or CF adjacent to the ear,
the eyes should not be blocked to light,
attachment should be soft and comfortable, and must not inflict injury,
attachment should not be permanent.

A preferred embodiment of the present invention provides a solution meeting all of the above-mentioned considerations by providing at least one attachment to the head that is located at the temples and forehead. Details of this preferred embodiment are described in reference to FIG. 5. Various components of the present invention provide a rigid mechanical structure represented by block 230. Details of how this function is provided are disclosed, inter alia, in reference to FIG. 5.

Various components of the present invention restrict the motion of the head in relation to the rest of the body of the patient. Details of how this function, represented by block 220, is provided are disclosed, inter alia, in reference to FIG. 6.

FIG. 3 schematically presents a situation in which the present invention is of practical use. A patient is depicted by head 310, jaw 360 and airways 320. The patient is depicted as being handled in order to open airways 320, and in particular, head 310 is depicted as being moved undesirably along arrow 350, while the jaw is being lifted. It is a benefit of the present invention that it restricts the movement of the head, while enabling the movement of the jaw.

FIG. 4 schematically presents the forces applied on a jaw, generally denoted by the numeral 400, as it is being forced open against resistance of the muscles. Various arrows depict the direction of forces extracted by various muscles, the sum of which is depicted by pair of lines 410. An external pair of forces directed to open the jaw in attachment to its two sides is depicted as pair of lines 420, and a single force directed to open the jaw in attachment to the chin is depicted as line 430. A first preferred embodiment of the present invention applies forces denoted by 420, and a second preferred embodiment of the present invention applies forces denoted by 430.

FIG. 5 schematically presents a structural part of a preferred embodiment of the present invention marked as part 500. Part 500 is designed to be located at the back of the head of the patient, and to attach to the head. It is an advantage of this preferred embodiment that this elongated part 500 is located at the back where it does not interfere with the functions of the eyes, nose, ears or mouth. Part 500 comprises the following rigid elements. Rigid element 510 is located at the back. A preferred embodiment for element 510 is disclosed herein below in reference to FIG. 14. Rigid elements located at the sides are collectively marked as 530. A preferred embodiment for element 530 is disclosed herein below in reference to FIG. 11 and FIG. 12. Alternative designs may be provided by persons skilled in the art, which employ rigid elements of varying shape and number to the same effect. Part 500 comprises soft elements providing comfort for the patient and avoiding injury. A preferred embodiment for soft elements is disclosed herein below in reference to FIG. 11. Part 500 comprises attachment elements as follows. An attachment element to the head is denoted by 550. In a preferred embodiment of the present invention it has roughly the shape of a part of an oval or a circle fitting the shape of the back of the head. In one embodiment of the present invention it is directly or permanently attached to the head by forehead strip and/or by other chemical or physical means.

A usually more desirable preferred embodiment does not employ such means, but comprises straps connecting to element 550 and wrapped around the forehead. Such straps are detailed herein below in reference to FIG. 10A. Part 500 comprises attachment element to the front 540, which attaches to the frontal parts of the present invention. Part 500 comprises attachment element to jaw related parts 590, which perform the function desired in reference to elastic block 240, e.g., a strip member in FIG. 1. A preferred embodiment for element 590 is disclosed herein below in reference to FIG. 17. Part 500 comprises attachment element to the rest of the body of the patient denoted by 560. The concentric circles depicted in FIG. 5 in relation to element 560 denote the generally round shape of this element in a preferred embodiment of the present invention.

FIG. 6 schematically presents a structural part of a preferred embodiment of the present invention marked as part 600. Part 600 is designed to be located at the front of the neck of the patient, and to support to the head, while allowing the airways to be opened by use of hole 610 and groove 620. Part 600 is essentially round to fit the shape of the neck. Groove 620 represents the essential feature in the present invention of allowing for movement of the jaw. Groove 620 is located just below the jaw. A first embodiment of the present invention lacks hole 610 to provide additional rigidity. A second embodiment of the present invention comprises hole 610 to allow cricothyroidotomy.

FIG. 7 schematically presents a structural part of a preferred embodiment of the present invention marked as part 700. Part 700 is designed to be attached to the jaw in a fitting fashion. It comprises elements that can move one in relation to the other and then lock in position. A detailed disclosure of part 700 and its elements is provided herein below in reference, inter alia, to FIG. 30A. Element 710 (left and right) fits the back of the jaw, and elements 720 (left and right) fit the front of the jaw. These elements can move one in relation to another. When part 700 is fitted to a specific jaw of a specific patient these elements are first moved so that a separating distance is created between them, then part 700 is placed under the jaw, and finally the elements of part 700 are moved so as to minimize the distance between them and thus achieve a tight fit to the jaw. FIG. 7 depicts a preferred embodiment of the present invention in which extrusion 750 provides the function of applying force and causing forward movement as described in reference to block 290 in FIG. 1. Preferably, 750 represents a pair of such extrusions at both sides of the jaw. Another embodiment of the present invention applies the forces denoted as 430 in reference to FIG. 4. It is acknowledged in this respect that aforementioned ingredients of the collar may be selected from elastic or non-elastic materials or any combination thereof (e.g., rigid members comprising elastic portions and vis versa).

Figure 8C:
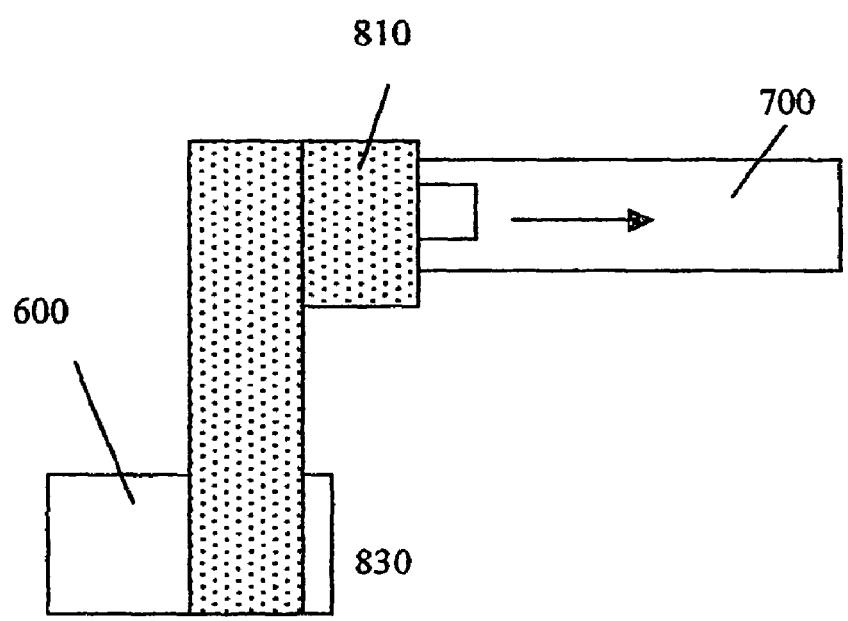

FIG. 8A, FIG. 8B and FIG. 8C schematically present some structural parts of a preferred embodiment of the present invention restricting and/or immobilizing the movement of the jaw. Strap or straps 820 move a pair of elements 810 forward through connecting element 830.

These elements perform the function described in reference to the lock member represented as block 250 in FIG. 1.

FIG. 8A shows element 600 described herein above in reference to FIG. 6, and the placement of elements 810 in relation to it.

FIG. 8B schematically describes a situation in which the jaw is being opened. Part 700 described in reference to FIG. 7 is moved, and is not essentially in contact with element 810.

FIG. 8C schematically describes a situation in which the jaw is being locked open. Part 700 described in reference to FIG. 7 essentially comes in contact with element 810, as element 810 is moved forward. A preferred embodiment of element 810 whose shape allows the movement described herein is disclosed in reference to FIG. 22 and FIG. 23.

Referring again to FIG. 8A, straps 820 secure element 810 in a jaw locking position when the movement terminates.

FIG. 9 schematically presents an element of a preferred embodiment providing the function of limiting the location of other moving elements. It is marked as the restriction member represented as block 260 in FIG. 1. Block 260 comprises an elastic band or strap, a ribbon, a string, a chain or essentially any flexible element attached to element 590 described in reference to FIG. 500 on one side, and to any location with in part 700 described in reference to FIG. 7 on another side.

FIG. 2 describes a preferred procedure for the use of a preferred embodiment of the present invention, an embodiment comprising essentially three parts: an anterior part as described in reference to FIG. 8A, a posterior part as described in reference to FIG. 5, and a jaw clasp as described in reference to FIG. 7. The procedure assumes an unconscious patient lying down, face up, as depicted in FIG. 3. Nevertheless, the terms front, back, up and down are used herein as if the patient was standing up, so for example, the posterior part can be said to be normally placed behind the anterior part rather the below it.

The procedure is as follows:

First, fit the posterior part by placing the posterior part behind the head of the patient, and shifting (2025) the part to the anatomically best fitting location. The part is preferable flexible to the extent that it may be folded (2010) and then straightened (2020) so that it is inserted (2015) behind the head of the patient without any need to move the head. Attach (2030) the part to the head by means of its attachment elements. One such attachment element is described herein below in reference to element 550 in FIG. 5. Attachment is preferably done above the eyes of the patient.

Second, fit the anterior part in front of the neck of the patient (2035), and attach it to the posterior part (2040). One such attachment element is described herein below in reference to element 540 in FIG. 5. Make sure (2045) the two parts form a tight fitting frame on the one hand, and that the patient is not being suffocated on the other hand. From this moment (2100) onwards, the anterior and posterior parts are referred to as one unified part and called the frame. From this moment onwards the invention is performing one of its two main functions, that of protecting the cervical spine.

Third, fit the jaw clasp. Enlarge it by displacing (2050) its elements, such elements as described herein below in reference to FIG. 7, so that the part becomes as large as possible. Connect (2055) the jaw clasp to the frame by elements described herein in reference to the restriction member represented as block 260 in FIG. 1; and retract (2060) elements of the frame that are normally in contact with the jaw clasp, elements described herein in reference to the lock member represented as block 250 in FIG. 1, so that said elements do not obstruct the placement of said jaw clasp.

Fit the part tightly to the jaw (2065), essentially reversing step 2050, and lock the tight fitting position of the elements of the jaw clasp. In a preferred embodiment of the present invention locking is achieved by means of a Velcro™-like strap described in reference to FIG. 30A herein below.

The invention is now fully assembled in place and ready to perform its other main function, that of opening the jaw or locking it in position (2200).

In a first embodiment of the present invention the invention is used to assist in performing the jaw-thrust maneuver. This essentially forward motion of the jaw is performed by moving elements described in reference to the lock member represented as block 250 in FIG. 1 forward. This motion is described herein below in reference to FIG. 8B. Locking the jaw is described in reference to element 820 in FIG. 8B.

In a second embodiment of the present invention the invention is also used to lock the jaw in an open position after a downward movement. This action is described in reference to FIG. 8C. Thus ends the procedure.

FIGS. 10A, 11B, 11, etc through FIG. 28 are a set of detailed technical drawings instructing a person skilled in the art how to manufacture a preferred embodiment of the present invention. These drawings are supplied so as to provide for a disclosure of the present invention that is full and detailed. However, the present invention is not limited to the exact shape, dimensions or materials disclosed in these figures.

FIGS. 10A, 10B, 10C, 11, 12, 13, 14, 15, 16 and 17 provide a detailed disclosure of the part labeled as 500 in reference to FIG. 5 as follows.

FIG. 10A shows the assembly of part 500. The figure shows various elements labeled 1 to 10, which are further described in the following figures. Elements labeled 8 and 9 comprise attachment straps made, for example, of Polypropylene. Strap 9 attaches to itself by means such as Veloro™-like tape. Strap 9 provides a preferred embodiment for element 530 as described in reference to FIG. 5. Strap 8 provides a preferred embodiment for element 540 as described in reference to FIG. 5.

Element labeled 10 in FIG. 10A is a loop around which strap 9 is laced in assembly.

FIG. 10B shows part 500 when fully assembled.

FIG. 10C comprises a table listing various elements of part 500 and disclosing their quantities, how many elements of each kind are required to assembled part 500.

FIG. 11 shows part 500, labeled 1 in FIG. 110A, along with its dimensions. The dimensions are suitable for an average patient, but different dimensions may suit different patients. One material suitable for making this element is plastazote foam, a type of polyethylene. This material is preferred as being soft, comfortable, lightweight, cheap, easy to mold to preferred shape, and transparent to X-ray radiation.

FIGS. 12 and 13 details a pair of elements of part 500 that is collectively labeled 530 in reference to FIG. 5. FIGS. 12 and 13 disclose 12 in a non-limiting manner one possible exact shape and dimensions for one embodiment of these elements. There is one such element, labeled 2 in FIG. 10A, fitted to the left of part 500, which is depicted in FIG. 12, and there is one such element labeled 3 in FIG. 10A, fitted to the right of part 500, which is depicted in FIG. 13.

FIG. 14 describes an element of part 500 that is labeled 510 in reference to FIGS. 5 and 4 in FIG. 10A. One material suitable for making element 510 and element 530 is ABS (Acrylonitrile Butadiene Styrene). This material is preferred for being rigid, light-weight, cheap, easy to mold to preferred shape, and transparent to X-ray radiation.

FIG. 15 describes a pin, labeled 5 in FIG. 10A, suitable for connecting soft or flexible elements of part 500. One material suitable for making this element is ABS.

FIG. 16 describes a nut, labeled 6 in FIG. 10A, suitable for connecting to the pin labeled 5 described in reference to FIG. 15. One material suitable for making this element is ABS.

FIG. 17 describes a hook labeled 7 in FIG. 10A. Its function is described as element 590 in reference to FIG. 5. One material suitable for making this element is ABS.

FIGS. 18A, 18B, 18C, 19, 20 and 21 provide a detailed disclosure of elements described in reference to FIGS. 8A, 8B and 8C as follows.

FIG. 18A shows the assembly of elements around part 600 described in reference to FIG. 6. The figure shows various elements labeled 1 to 9, which are further described in the following figures. Element labeled 7 comprises a strap similar but complementary to element labeled 8 in FIG. 10A. Strap 7 of FIG. 18A and strap 8 of FIG. 10A connect and attach to each other by means such as Velcro™-like tape to provide the connection between part 600 and part 500 of the present invention. Element labeled 8 comprises a strap similar to element labeled 9 in FIG. 10A. This strap is a preferred embodiment of element 820 described in reference to FIG. 8A. Nails labeled as 4 are preferably made of plastic materials are connecting straps to other rigid elements of this assembly. Loop labeled 9 connected to other parts by these nails is a preferred embodiment of element 830 described in reference to FIG. 8.

FIG. 18B shows the same elements when fully assembled.

FIG. 18C comprises a table listing various elements described in FIG. 18A and disclosing their quantities per one unit of assembled part of the present invention.

FIG. 19 shows part 600, labeled 1 in FIG. 18A, along with its dimensions. The dimensions are suitable for an average patient, but different dimensions may suit different patients. It is made from materials similar to those of part 500 as described in reference to FIG. 11.

FIGS. 20 and 21 details a pair of elements that are collectively labeled 810 in reference to FIG. 8A. FIGS. 20 and 21 disclose the exact shape and dimensions for one embodiment of these elements. There is one such element, labeled 2 in FIG. 18A, fitted to the left of part 600, which is depicted in FIG. 12, and there is one such element labeled 3 in FIG. 18A, fitted to the right of part 600, which is depicted in FIG. 13. In reference to FIGS. 20 and 21 it is evident how the shape of elements 810 allow them to slide backwards or forwards as schematically depicted in FIG. 8C.

FIGS. 22A, 22B, 22C, 23A, 23B, 24A, 24B, 25A, 25B, 26A, 26B, 27 and 28 provide a detailed disclosure of part 700 described in reference to FIG. 7 herein above.

FIG. 22A shows the assembly of part 700. The figure shows various elements labeled 1 to 10, which are further described in the following figures. Elements labeled 8 and 9 are similar in form and function to corresponding elements described in reference to FIG. 10A and FIG. 18A. Element labeled 7 provides a preferred embodiment of the restriction member represented as block 260 described in reference to FIG. 1, and implemented by means of a rubber band. Element labeled 10 is not shown as it would obscure other elements. It is comprised of soft sponge like padding covering the assembled part for comfort and prevention of injury.

FIG. 22B shows the same elements when fully assembled, and depicts how they may be moved one in relation to another.

FIG. 22C comprises a table listing various elements described in FIG. 22A and disclosing their quantities per one unit of assembled part of the present invention.

Figure 23A:
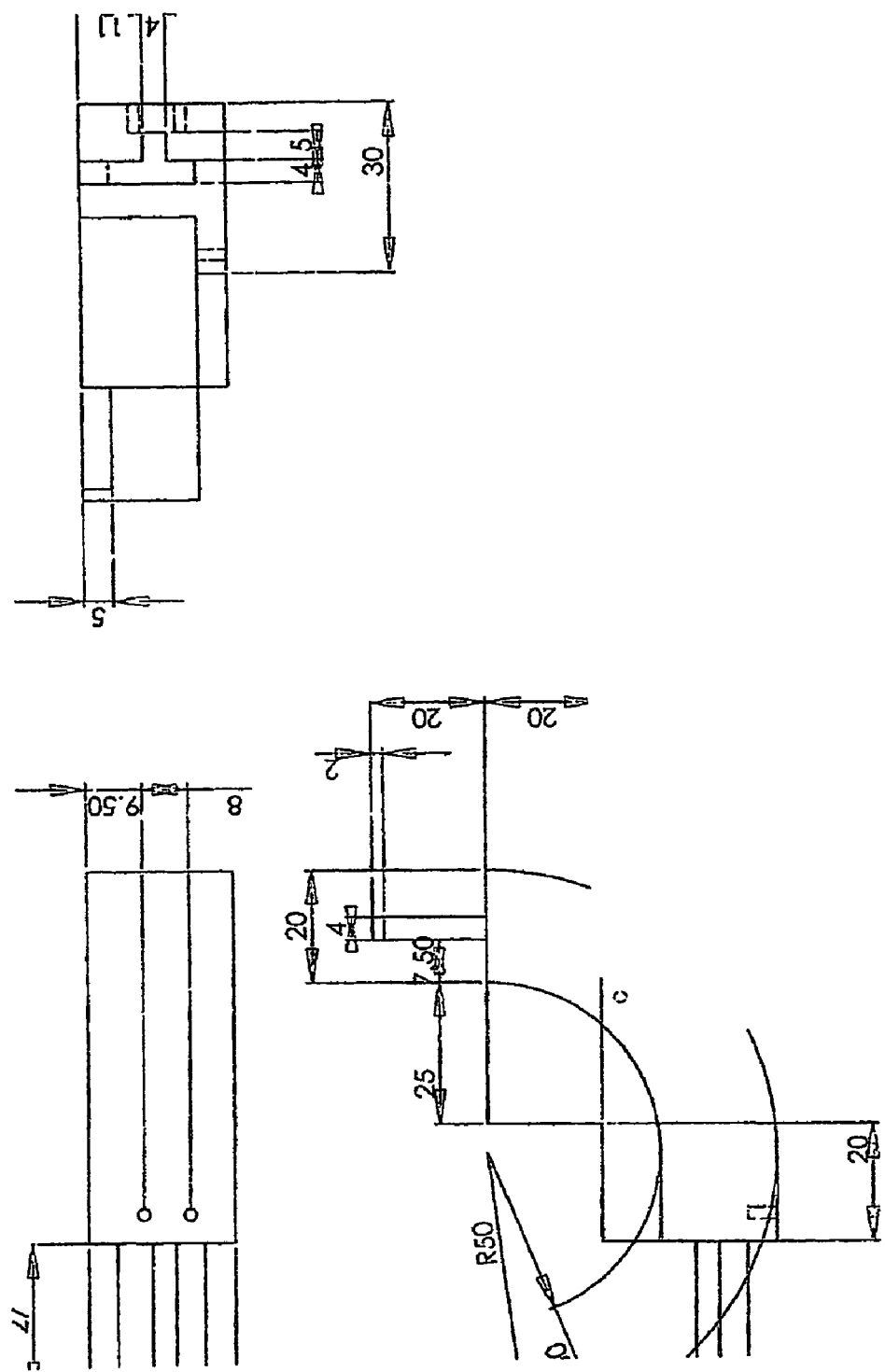
Figure 24A:
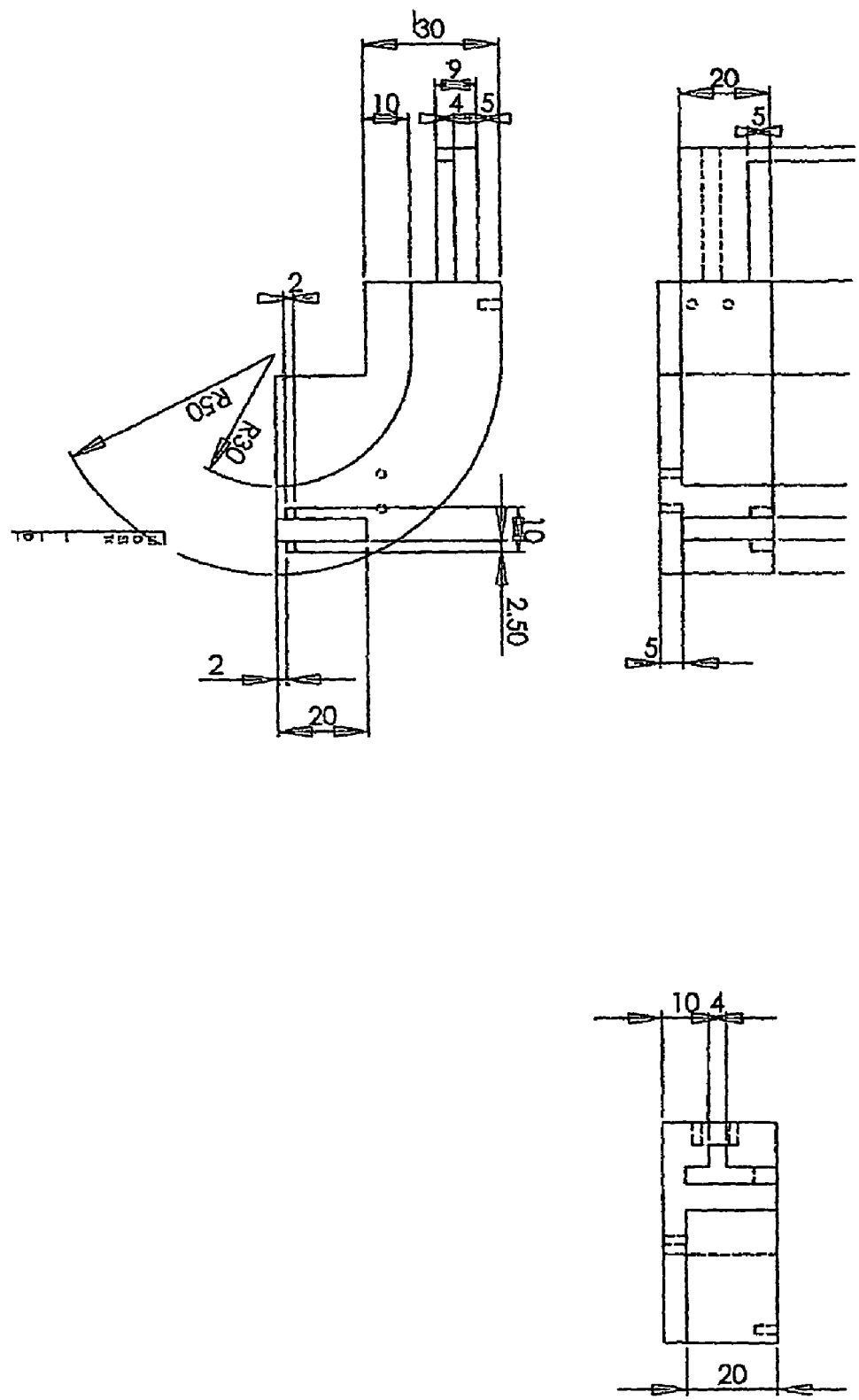

FIGS. 23A, 23B, 24A and 24B detail a pair of elements that are labeled 1 and 2 in FIG. 22A and collectively labeled 720 in reference to FIG. 7. FIGS. 23A, 23B, 24A and 24B disclose in a non-limiting manner one possible exact shape and dimensions for one embodiment of these elements. The right element is depicted in FIG. 23A and FIG. 23B, and the left element is depicted in FIGS. 24A and 24B. These elements are preferably made of material such as that described in reference to FIG. 14.

Figure 25B:
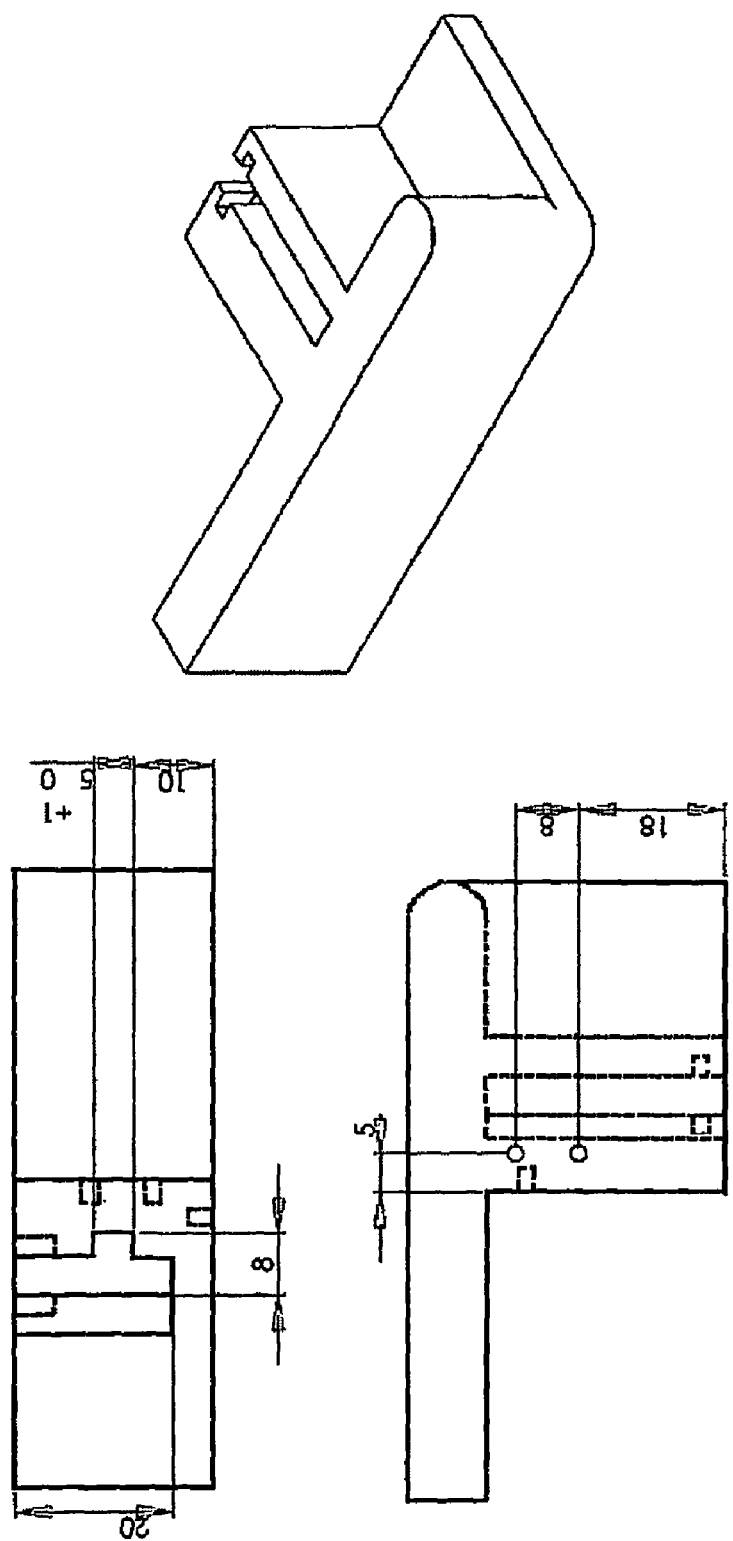

FIGS. 25A, 25B, 26A and 26B detail a pair of elements that are labeled 3 and 4 in FIG. 22A and collectively labeled 710 in reference to FIG. 7. FIGS. 25A, 25B, 26A and 26B disclose the exact shape and dimensions for one embodiment of these elements. The right element is depicted in FIG. 25A and FIG. 25B, and the left element is depicted in FIGS. 26A and 26B. These elements are preferably made of material such as that described in reference to FIG. 14.

FIG. 27 details an element labeled 5 in FIG. 22A for a locking rail on which other elements move one in respect to another. It is preferably made of material such as that described in reference to FIG. 14.

FIG. 28 details a nail labeled 6 in FIG. 22A for attaching straps to other parts of the assembly. It is preferably made of material such as that described in reference to FIG. 14.

Reference is made now to FIG. 29-32 presenting a plurality of further embodiments according to the present invention, described and defined hereinafter assembled view of the novel cervical collar.

FIG. 29 details a cervical collar comprising a 'jaw thrust'-like knob maneuvering the mandible according to yet one embodiment of the present invention. Said jaw thrust is provided by a means of an adjustable knob (1290) comprising an inside portion facing the angels of the mandible as holding points and an outside portion maneuverable by the care giver.

The inside portion comprising a rest (291) and a bolt (292), such that an accommodating-pushing groove (293) is provided. The accommodating-pushing groove (293) is adapted to concurrently accommodating the mandible angle while pushing it anteriorly towards the direction of the chin, i.e., in the opposite direction of cervical spin.

The outside portion comprising adjustable knob (295) moving reversibly along recess (294) and is in communication with the inside portion by means of a pin (296). Said pin (296) and knob (295) is freely moving anteriorly (i.e., frontally) in recess (294) such that the care giver can fix it in the recess such that the mandible is pushed anteriorly enough to ensure open airway, then the pin (296) is securable fastened by any fastening means, such as screws, claspers, fasteners, fetters, handcuffs-like members etc. The anchoring of the knob, after it was fixed at the right location, is against the collar. The posterior part of the collar is composed of stiff material (such plastic), which according to another embodiment of the present invention can be adjustable to the patent by getting change around some pivot.

It is further in the scope of the present invention wherein the caregiver steps are (a) fixing the collar on the patient, then executing the jaw thrust maneuver, (b) using the knob to push the mandible angle, wherein the push of the knob is carried by the thumbs while the index fingers are leaning on the patent's Zygoma (maxilla), and (c) repeating the same maneuvers as the caregiver would do if he did a jaw thrust maneuver without using the collar.

FIG. 30 details a cervical collar comprising a 'chin lift' collar 1310 according to yet one embodiment of the present invention wherein holding point is the chin, gum, or any other member of the oral cavity (1316). The chin lift is holding the chin and then pushing it anteriorly while it is being supported on the sternal bone, the maxilla, the zygoma or any other ingredients of the collar. Said lever comprises rear portion (1310) and frontal portion (1312). Said frontal portion includes said 'chin lift' lever (1314) in communication with belt (1313) by means of hinge (1315). Lever (1314, 1314*a*) is adapted for a lifting the chin (1316) and the mandible thereof.

FIG. 31 details both lifted chin conformation of lever (1314, 1314*a*) and its un-lifted chin conformation. It is acknowledged in this respect that more embodiments of the 'chin lift' lever are possible. Hence, it is in the scope of the present invention wherein lever (1314, 1314*a*) is adapted to grasp body portion (1316) and push it upwardly/anteriorly.

FIG. 32 details another embodiment of the present invention, wherein a maxillary support is provided. Said device comprising anchoring belt (3220) and two claspers (3221)

adapted for concurrently accommodating the angles of the mandible as holding points, while pushing it anteriorly towards the direction of the chin. The fixation of the belt at the right location is accomplished in the same way as in the aforesaid 'jaw thrust' embodiment, or by fixing the belt (3220) and two claspers (3221) in there required position.

The invention claimed is:

1. A method for performing a device aided jaw-thrust maneuver on a patient that is immobilized with a cervical collar, said method comprising:
   a. providing a cervical collar comprising: (i) a rigid motion-restricting frame attachable to the head for restricting the motion of the head in relation to the rest of the body of said patient, (ii) a jaw clasp attachable to the jaw of said patient, (iii) a restrictor member for restricting the distance and the direction of motion of said jaw clasp relative to said rigid motion-restricting frame, and (iv) a lock member preventing backward motion of said jaw clasp relative to said rigid motion-restricting frame;
   b. restricting the motion of the head and neck of said patient via the rigid motion-restricting frame;
   c. clasping an external portion of the jaw with said jaw clasp;
   d. maneuvering the jaw via said jaw clasp in a forward and slightly downward manner;
   e. simultaneously restricting the distance in the direction of motion of said jaw clasp relative to said rigid motion-restricting frame by said restrictor member; and
   f. simultaneously preventing backward motion of said jaw clasp relative to said rigid motion-restricting frame by said lock member;
   wherein said steps (b)-(f) restrict the motion of the head and neck of the patient while simultaneously maintaining open the airway of the patient.

2. The method according to claim 1, wherein said cervical collar is adapted for maintaining open airways in the head and neck of the immobilized trauma patient and for simultaneously restricting the motion of the head and neck while allowing motion of the jaw to maintain open the airways, and
   wherein said collar is adapted for restricting the motion of the head and neck, while simultaneously maneuvering said jaw clasps attached to the jaw, in a forward and slightly downward direction such that airway maintenance with cervical spin control is provided.

3. The method according to claim 1, comprising:
   a. fitting a first part of said cervical collar;
   b. fitting a second part of said cervical collar;
   c. fitting a third part of said cervical collar; and,
   d. using said third part to perform a jaw-thrust maneuver.

* * * * *